(12) United States Patent
Sauer

(10) Patent No.: US 12,364,483 B2
(45) Date of Patent: Jul. 22, 2025

(54) MINIMALLY INVASIVE OCCLUSION DEVICE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 18/209,787

(22) Filed: Jun. 14, 2023

(65) Prior Publication Data

US 2023/0338030 A1 Oct. 26, 2023

Related U.S. Application Data

(63) Continuation of application No. 17/030,568, filed on Sep. 24, 2020, now Pat. No. 11,717,301.

(60) Provisional application No. 62/916,561, filed on Oct. 17, 2019, provisional application No. 62/905,854, filed on Sep. 25, 2019.

(51) Int. Cl.
*A61B 17/12* (2006.01)
*A61B 17/00* (2006.01)
*A61B 17/122* (2006.01)
*A61B 17/128* (2006.01)

(52) U.S. Cl.
CPC ...... *A61B 17/12013* (2013.01); *A61B 17/122* (2013.01); *A61B 17/1285* (2013.01); *A61B 2017/00907* (2013.01)

(58) Field of Classification Search
CPC ......... A61B 17/122–1285; A61B 2017/00243; A61B 17/12
USPC ........................................ 606/142, 143, 144
See application file for complete search history.

(56) References Cited

U.S. PATENT DOCUMENTS

| | | |
|---|---|---|
| 6,626,922 B1 | 9/2003 | Hart et al. |
| 6,916,332 B2 | 7/2005 | Adams |
| 8,465,507 B2 | 6/2013 | Cosgrove et al. |
| 8,636,754 B2 | 1/2014 | Hughett, Sr. et al. |
| 8,852,218 B2 | 10/2014 | Hughett, Sr. et al. |
| 8,998,935 B2 | 4/2015 | Hart |
| 9,017,349 B2 | 4/2015 | Privitera et al. |
| 9,078,687 B2 | 7/2015 | Rohaninejad et al. |
| 9,119,627 B2 | 9/2015 | Cosgrove et al. |
| 9,265,486 B2 | 2/2016 | Hughett, Sr. et al. |
| 9,282,973 B2 | 3/2016 | Hughett, Sr. et al. |
| 9,486,225 B2 | 11/2016 | Michler et al. |

(Continued)

OTHER PUBLICATIONS

International Search Report and Written Opinion for International Application No. PCT/US21/51860, filed Sep. 24, 2021, mailed Feb. 7, 2022, 10 pages.

*Primary Examiner* — Kathleen S Holwerda
*Assistant Examiner* — Serenity A Miller
(74) *Attorney, Agent, or Firm* — Michael E. Coyne

(57) ABSTRACT

A minimally invasive occlusion device is disclosed. The minimally invasive occlusion device includes a first link having a first end and a second end, a second link having a first end and a second end; the first end of the second link connected to the first end of the first link by a compensating coupler. Another minimally invasive occlusion device may include a delivery frame or a shaft having an articulating cradle coupled to the shaft. A method of occluding tissue is also disclosed. The method of occluding tissue includes placing a first link of an occlusion device laterally at a base of tissue, placing a second link of an occlusion device on an opposing side of the base of tissue, substantially parallel with the first link, and securing the first link and the second link to fully occlude the base of tissue.

5 Claims, 33 Drawing Sheets

(56) References Cited

U.S. PATENT DOCUMENTS

| | | |
|---|---|---|
| 9,668,671 B2 | 6/2017 | Friedman et al. |
| 9,808,257 B2 | 11/2017 | Armenteros et al. |
| 9,861,371 B2 | 1/2018 | Martin et al. |
| 9,883,863 B2 | 2/2018 | Hughetti, Sr. et al. |
| 9,883,867 B2 | 2/2018 | Martin et al. |
| 9,888,925 B2 | 2/2018 | Bertolero et al. |
| 9,901,351 B2 | 2/2018 | Winkler et al. |
| 9,901,352 B2 | 2/2018 | Fago et al. |
| 10,064,623 B2 | 9/2018 | Soutorine et al. |
| 10,925,615 B2 | 2/2021 | Deville et al. |
| 2006/0020271 A1 | 1/2006 | Stewart et al. |
| 2008/0294175 A1 | 11/2008 | Bardsley et al. |
| 2010/0179570 A1 | 7/2010 | Privitera et al. |
| 2010/0204716 A1 | 8/2010 | Stewart et al. |
| 2012/0035631 A1 | 2/2012 | Hughett, Sr. et al. |
| 2015/0257756 A1 | 9/2015 | Sauer |
| 2019/0231356 A1 | 8/2019 | Deville et al. |
| 2019/0262135 A1 | 8/2019 | Sauer |
| 2020/0107835 A1 | 4/2020 | Sauer |

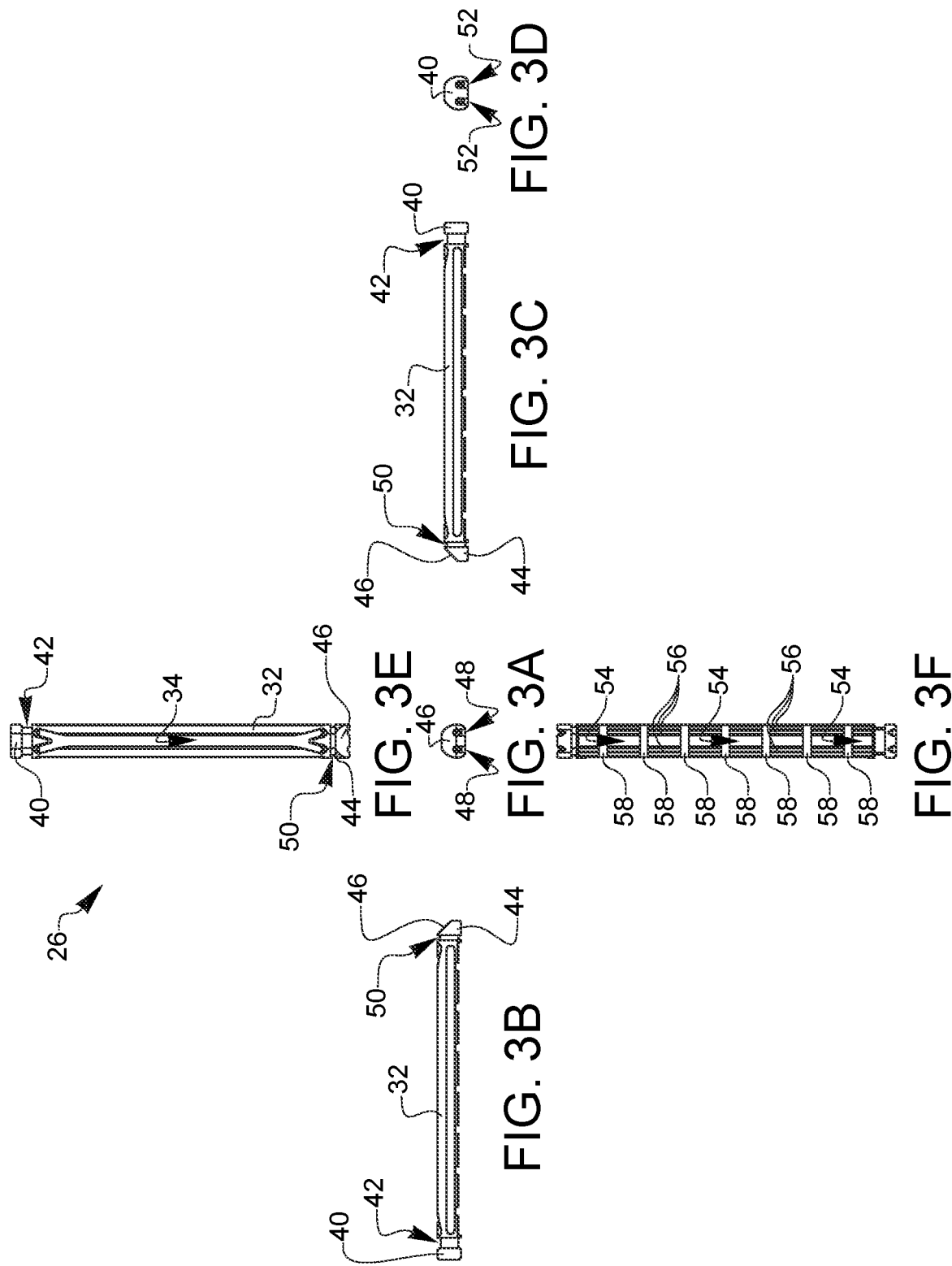

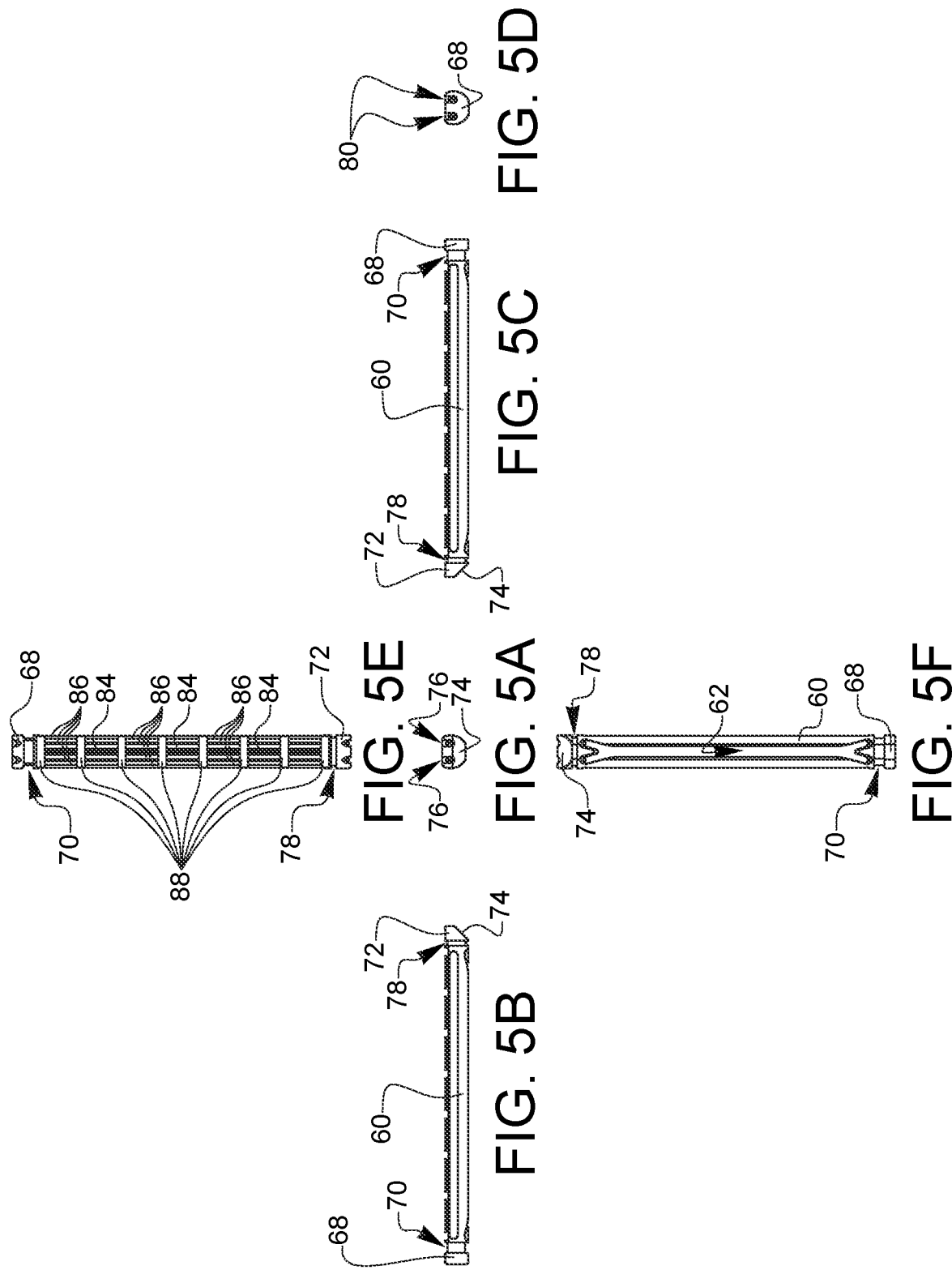

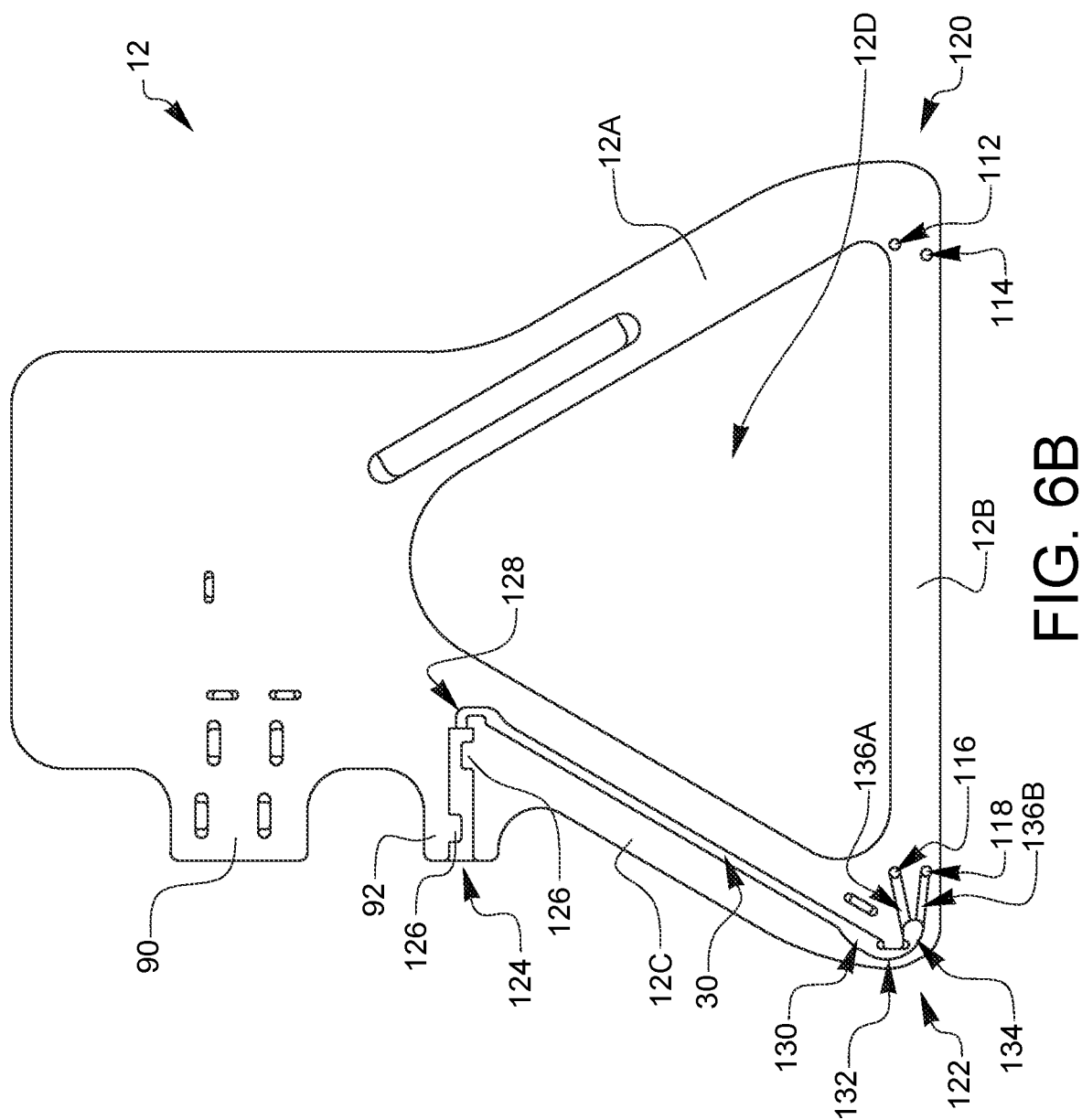

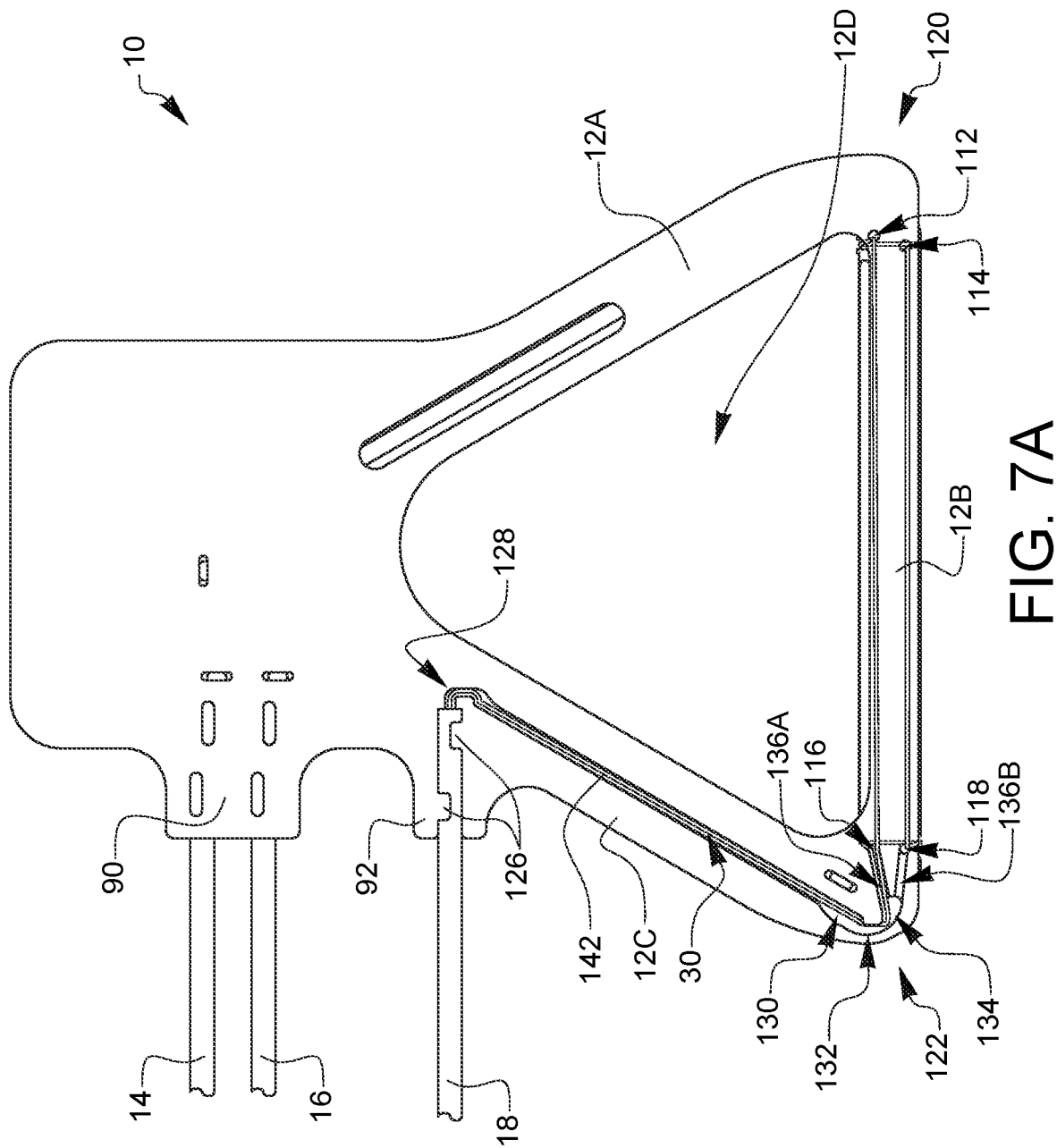

MINIMALLY INVASIVE OCCLUSION DEVICE AND METHODS THEREOF

REFERENCE TO RELATED APPLICATIONS

This patent application is a continuation of U.S. patent application Ser. No. 17/030,568, filed on Sep. 24, 2020, which claims priority to U.S. Provisional Patent Application No. 62/905,854, filed Sep. 25, 2019, and U.S. Provisional Patent Application No. 62/916,561, filed Oct. 17, 2019, each of which are hereby incorporated by reference in their entirety.

FIELD

The claimed invention relates to devices used for the occlusion of anatomical structures, and more specifically to minimally invasive surgical devices used for the occlusion of anatomical structures such as the left atrial appendage.

BACKGROUND

Atrial fibrillation (AF) is a common cardiac arrhythmia affecting millions of people and is associated with ischemic stroke, increasing the risk for stroke by as much as five-fold for patients with atrial fibrillation (AF). AF leads to insufficient contraction of the left atrium, lowered endurance, and irregular heartrate. The inactivity of sufficient blood flow within the left atrium leads to hypercoagulability and thus to an increased risk for thrombus formation. Left atrial appendage thrombosis and embolization is recognized as the principal mechanism of stroke related to AF. This stroke mechanism can be correlated with reduced LAA flow velocity, thrombus formation, hypertension, and atheromatous disease of the aorta. The left atrial appendage (LAA) is an accessory chamber of the heart extending over an area of 3 to 6 $cm^2$, that fills and empties in response to both ventricular and atrial dynamics. Variable morphology of the left atrial appendage with respect to shape, volume, length, and width, specifically, larger LAA volume, depth, and number of lobes may be related to likelihood of thrombus formation.

At present, pharmacological based anticoagulation therapy, particularly with warfarin, is recognized as a highly effective treatment for medical management of patients with AF. While highly effective, warfarin use has a narrow therapeutic range and is associated with a potential risk of major hemorrhage and pharmacological contraindications. When these risks or other impediments to anticoagulation outweigh the risk of stroke related to AF, removing or isolating the LAA may be an attractive alternative approach for the prevention of embolic events.

Occluding the LAA from communication with the left atrium at the time of other cardiac surgery is relatively straightforward. The LAA can be occluded surgically by ligation, plication, or amputation, a procedure which can be performed routinely in patients as an adjunct to heart valve surgery. Transvenous occlusion of the LAA is also a known approach in preventing embolism in patients with AF, utilizing catheter deployment of an implantable device to seal the mouth of the LAA. Percutaneous LAA occlusion is another known approach for occluding the LAA from blood flow and thus preventing thrombus formation and subsequent thromboembolic complications. The advantages of the percutaneous LAA occlusion technique include a less invasive procedure, a faster recovery as compared with surgical ligation, and the reduced risk of potential bleeding in the absence of anticoagulation therapy. However, occlusion of the LAA remains challenging. While novel approaches to LAA occlusion have been developed, they can be more complex and may potentially have increased risks of LAA injury, incomplete occlusion, and device dislocation.

Therefore, it would be desirable to have a reliable device for occlusion of the left atrial appendage as well as associated methods thereof. Ideally, such a device and method would be minimally invasive yet be deliverable via open sternotomy, right lateral thoracotomy or sub-xiphoid access. It would also be desirable for an occlusion device offering higher efficacy in terms of higher rates for successful long-term occlusion, ease of use, improved accommodation of individual anatomical variations, as well as having the ability to reposition the device if initial delivery and placement was deemed inadequate. Faster and more reliable cardiac operations offer additional benefits, such as reduced surgical team fatigue and more efficient use of critical resources. Expediting cardiac surgery can also improve patient outcomes.

SUMMARY

A minimally invasive occlusion device is disclosed. The minimally invasive occlusion device includes a first link having a first end and a second end, a second link having a first end and a second end; the first end of the second link connected to the first end of the first link by a compensating coupler.

Another minimally invasive occlusion device is disclosed. The minimally invasive occlusion device may include a delivery device. This minimally invasive occlusion device may include a delivery frame. The minimally invasive occlusion device may include a shaft and an articulating cradle coupled to the shaft. The minimally invasive occlusion delivery device may include a shaft, a first jaw coupled to the shaft, and a second jaw coupled to the shaft.

A method of occluding tissue is disclosed. The method of occluding tissue includes placing a first link of an occlusion device laterally at a base of tissue, placing a second link of an occlusion device on an opposing side of the base of tissue, substantially parallel with the first link, and securing the first link and the second link to fully occlude the base of tissue.

BRIEF DESCRIPTION OF THE DRAWINGS

FIGS. 3A, 3B, 3C, 3D, 3E, and 3F are front, left side, right side, rear, top, and bottom elevational views, respectively, of the top mobile link of FIGS. 2A and 2B.

FIGS. 5A, 5B, 5C, 5D, 5E, and 5F are front, left side, right side, rear, top, and bottom elevational views, respectively, of the bottom tethered link of FIGS. 4A and 4B.

FIGS. 6A-6B are front and back views, respectively, of a delivery frame of the minimally invasive occlusion device of FIG. 1.

FIGS. 7A, 7B, and 7C are back, front, and front views, respectively, of the minimally invasive occlusion device of FIG. 1 illustrating various filament threading paths.

Figure 1A:
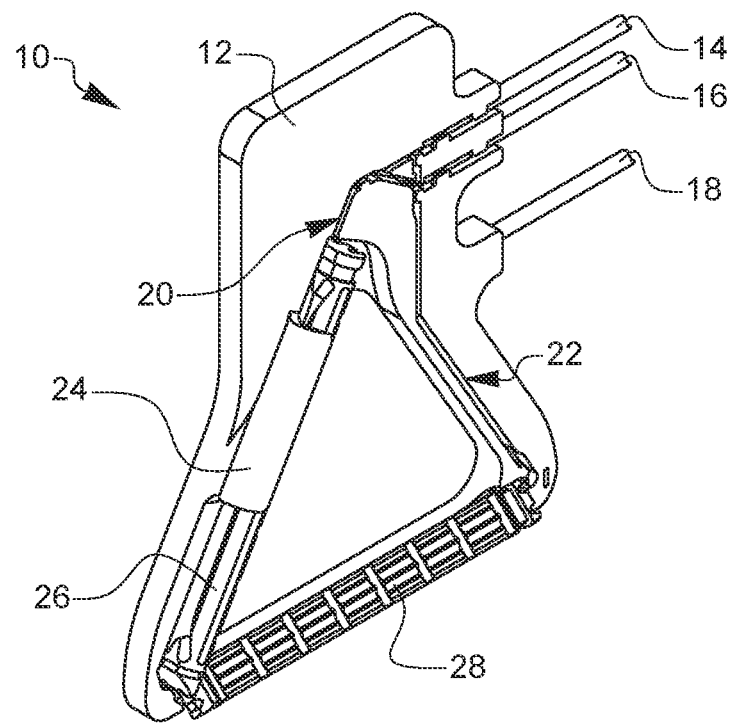
FIGS. 1A and 1B are top left front and top right back perspective views, respectively, of an embodiment of a minimally invasive occlusion device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
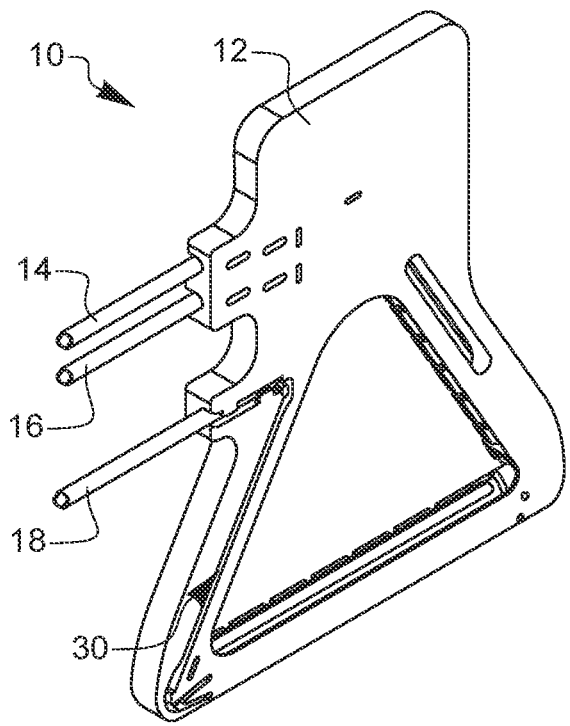

FIGS. 1A and 1B are top left front and top right back perspective views, respectively, of an embodiment of a minimally invasive occlusion device. FIG. 1A is a top left front perspective view of an embodiment of a minimally invasive occlusion device 10. The minimally invasive occlusion device 10 includes a delivery frame 12 which is molded from a plastic translucent material. The delivery frame 12 defines a half cover or holder 24 which releasably holds a first mobile link 26, a first filament channel 20, and a second filament channel 22. A second tethered link 28 is also held to the frame by a suture, which is not visible here, but will be discussed later. A first filament lumen 14, a second filament lumen 16, and a third filament lumen 18 are also held in the delivery frame 12 of the minimally invasive occlusion device 10. The first filament channel 20 and the second filament channel 22 are defined by the delivery frame 12 and are configured to hold and guide a filament, suture, or wire through the delivery frame 12 and through the mobile link 26 and the tethered link 28 until the minimally invasive occlusion device 10 is deployed. FIG. 1B is a top right back perspective view of the minimally invasive occlusion device of FIG. 1A. The delivery frame 12 of the minimally invasive occlusion device 10 defines a third filament channel 30. This third filament channel 30 is also configured to hold and guide a filament, suture, or wire through the delivery frame 12 and around the tethered link 28 until the minimally invasive occlusion device 10 is deployed.

While this embodiment of a minimally invasive occlusion device 10 is shown in FIGS. 1A and 1B, alternate embodiments of such a minimally invasive occlusion device may have different sizes to accommodate normal variations in size of a left atrial appendage in various patients. The delivery frame, which may also be referred to as a delivery card, is shown as substantially triangular in shape in FIGS. 1A and 1B. Alternate embodiments of a minimally invasive occlusion device 10 may be shaped differently, such as square, rectangular, trapezoidal, or even combinations thereof. Furthermore, although this embodiment of a minimally invasive occlusion device has a delivery frame molded from a translucent plastic material to enable or improve visualization through the frame during a minimally invasive occlusion procedure, alternate embodiments may have delivery frames made from other materials such as stainless steel or other suitable metals or molded from plastic composites or other suitable plastic materials. Furthermore, translucent plastics may include a transparent material, partially transparent plastics, and dyed or colored plastics. Suitable frame materials may include polycarbonate, polymethylmethacrylate, acrylic, polyethylene terephthalate (PET), amorphous copolyester (PETG), polyvinyl chloride (PVC), liquid silicone rubber (LSR), cyclic olefin copolymers, polyethylene (PE), and combinations thereof. Sutures may also be referred to as tensioning members, tensioning filaments, wires, and the like. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

Figure 2A:
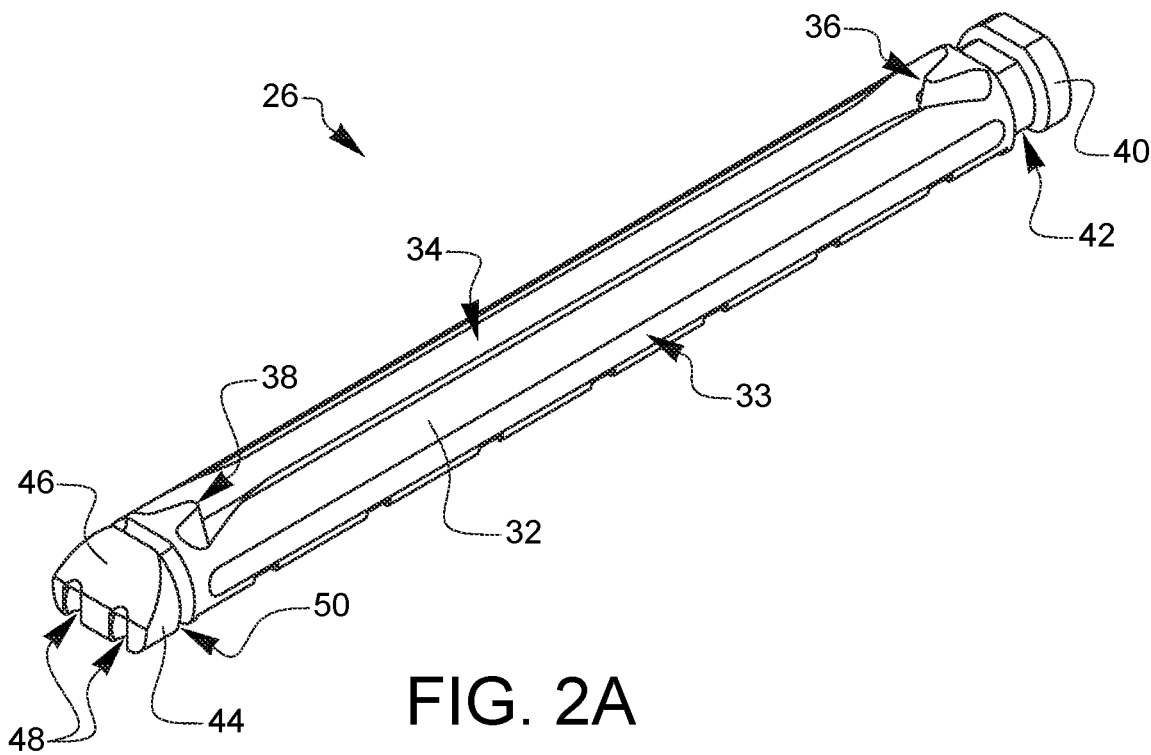
FIGS. 2A and 2B are perspective views of a top mobile link of the minimally invasive occlusion device of FIG. 1.
Figure 2B:
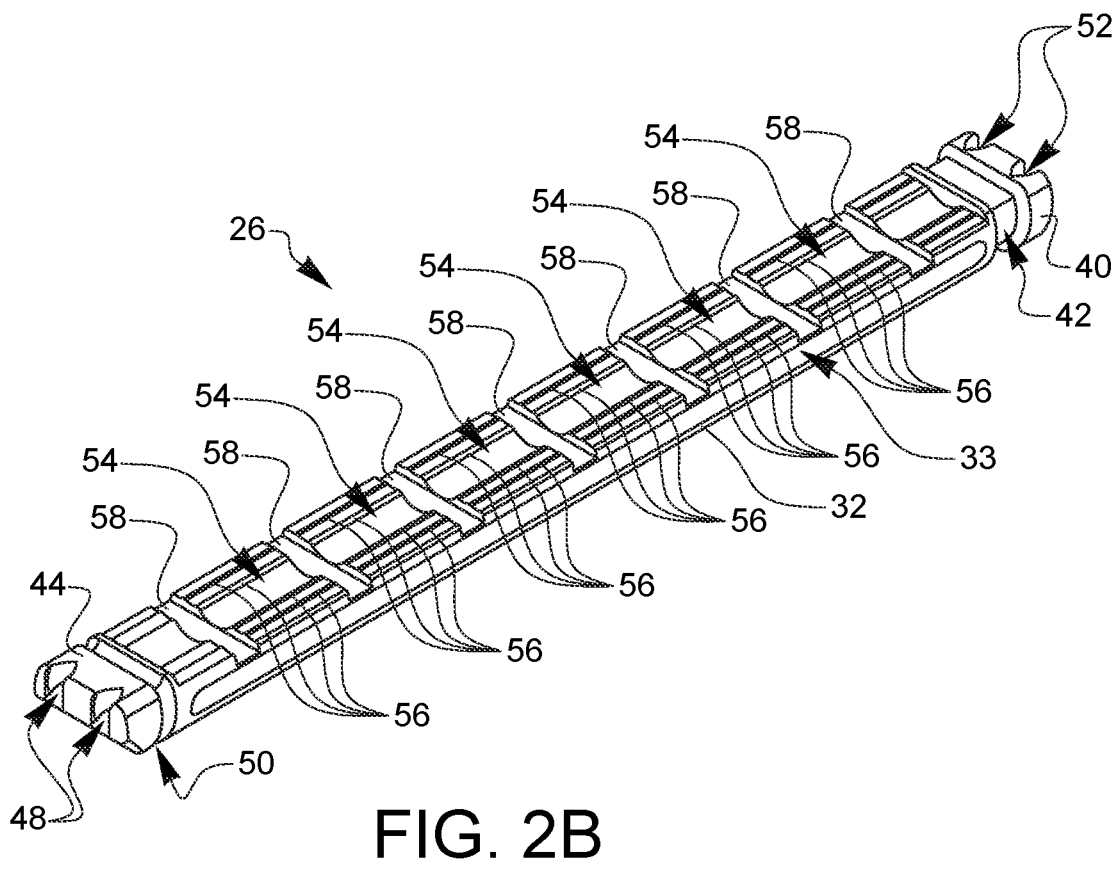

FIGS. 2A and 2B are perspective views of a top mobile link of the minimally invasive occlusion device of FIG. 1. FIG. 2A is a bottom perspective view of a first, top mobile link of the minimally invasive occlusion device of FIG. 1. The mobile link 26 is a singular, monolithic link defining a cap 40 at one end, a beveled cap 44 at an opposite end, connected by a beam 32. The cap 40 also defines two filament apertures 52. The beveled cap 44 further defines a bevel 46 and two filament apertures 48. Next to the cap 40 is a circumferential recess 42, and next to the beveled cap 44 is a circumferential recess 50. The two circumferential recesses 42, 50 are configured to hold and guide a tether filament or suture, which is not shown here but will be discussed later. Within the beam 32 there is a beam recess 33 on either side and a filament channel 34 which has a bifurcation 36 adjacent to the circumferential recess 42 next to the cap 40 and a bifurcation 38 adjacent to the circumferential recess 50 next to the beveled cap 44. The filament channel 34 is configured to hold and guide one or more sutures or filament within the longitudinal length of the mobile link 26 and is in communication from the two filament apertures 52, through the bifurcation 36, through the filament channel 34, through bifurcation 38, and through filament apertures 48. The bifurcations 36, 38 at either end of the mobile link 26 are configured to encourage two separate filaments to freely travel and move longitudinally throughout the mobile link 26. While there may be contact between two separate filaments threaded through the filament channel 34 of the mobile link 26, the divergent structure of the bifurcations 36, 38 towards the caps 40, 44 will limit tangling and frictional sticking between two filaments, allowing multiple filaments or sutures within the channel 34 to slide in a longitudinal direction while the occlusion device and its mobile link 26 and tethered link 28 are being placed, adjusted, and tightened.

FIG. 2B is a top perspective view of the first, top mobile link of FIG. 2A. FIG. 2B illustrates the respective locations of the filament apertures 52 of the cap 40, the filament apertures 48 of the beveled cap 44, as well as additional features from the top perspective of the mobile link 26. The top surface of the mobile link 26 defines a center recess 54, several ridges 56 on either side of the center recess 54, and several interstitial recesses 58 perpendicular to the center recess 54 and ridges 56. These features combine to form a gripping surface resulting in opposing interdigitating surfaces on the mobile link 26 that correspond and interlock with similar features on the top surface of the bottom tethered link. While the links shown in FIGS. 2A and 2B are substantially cylindrical, other embodiments of links may be more or less rounded, rectangular, tubular, or flat relative to the embodiment shown herein. FIGS. 3A, 3B, 3C, 3D, 3E, and 3F are front, left side, right side, rear, top, and bottom elevational views, respectively, of the top mobile link of FIGS. 2A and 2B. Alternate embodiments of a top mobile link may have alternate lengths to accommodate anatomical variations or other sizing considerations related to left atrial appendages or other anatomical tissue structures.

Figure 4A:
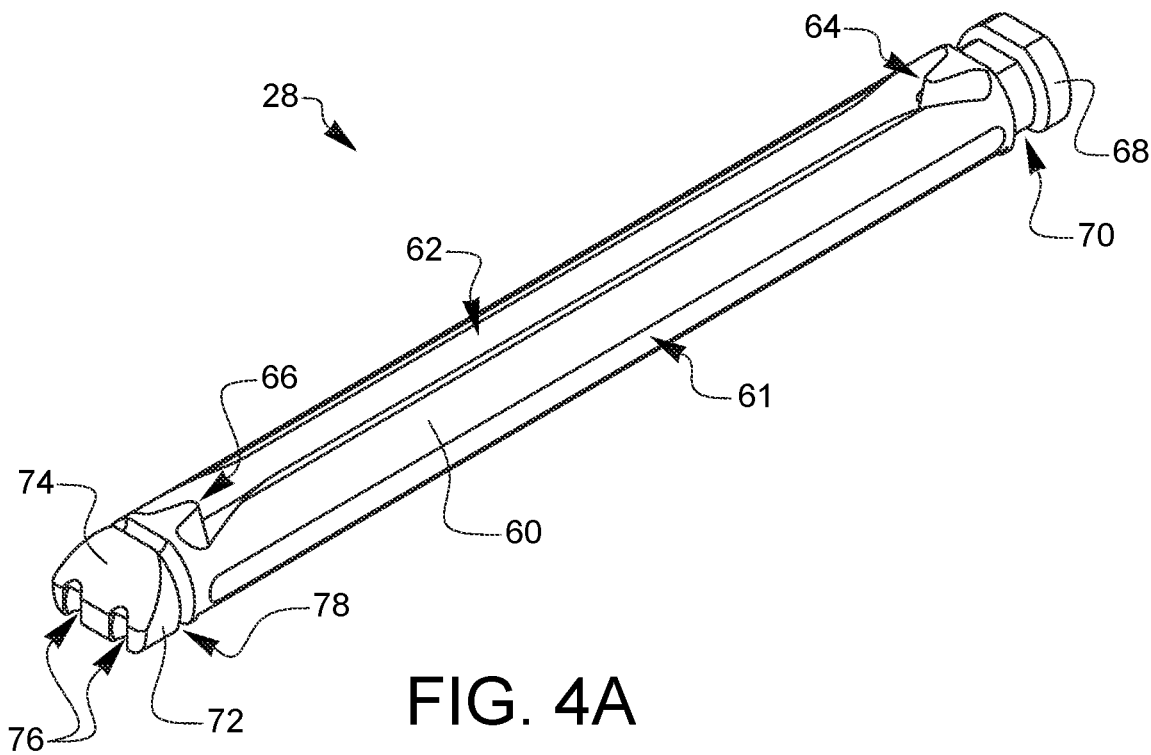
FIGS. 4A and 4B are perspective views of a bottom tethered link of the minimally invasive occlusion device of FIG. 1.
Figure 4B:
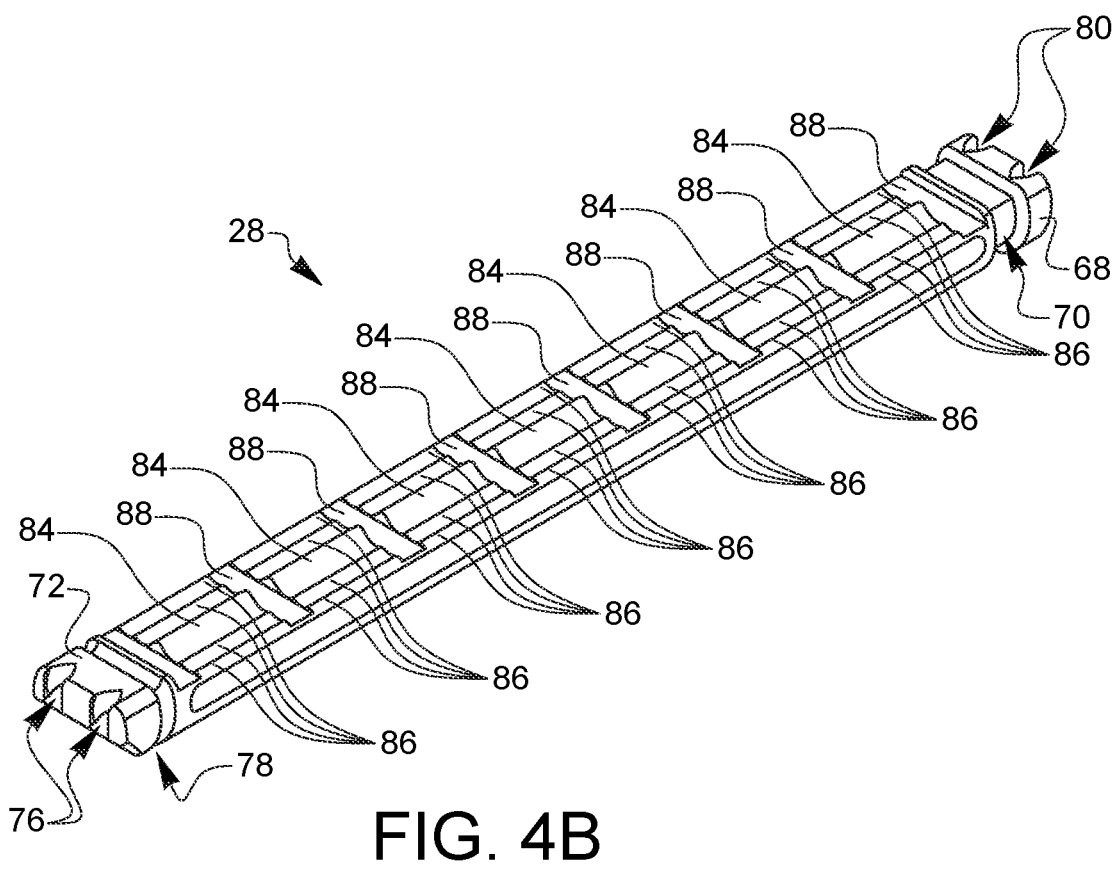

FIGS. 4A and 4B are perspective views of a bottom tethered link of the minimally invasive occlusion device of FIG. 1. FIG. 4A is a bottom perspective view of a second, bottom tethered link of the minimally invasive occlusion device of FIG. 1. The tethered link 28 is a singular, monolithic link defining a cap 68 at one end, a beveled cap 72 at an opposite end, connected by a beam 60. The cap 68 also defines two filament apertures 80. The beveled cap 72 further defines a bevel 74 and two filament apertures 76. Next to the cap 68 is a circumferential recess 70, and next to the beveled cap 72 is a circumferential recess 78. The two circumferential recesses 70, 78 are configured to hold and guide a tether filament or suture, which is not shown here but will be discussed later. Within the beam 60 there is a beam recess 61 on either side and a filament channel 62 which has a bifurcation 64 adjacent to the circumferential recess 70 next to the cap 68 and a bifurcation 66 adjacent to the circumferential recess 78 next to the beveled cap 72. The filament channel 62 is configured to hold and guide one or more sutures or filament within the longitudinal length of the tethered link 28 and is in communication from the two filament apertures 80, through the bifurcation 64, through the filament channel 62, through bifurcation 66, and through filament apertures 76. The bifurcations 64, 66 at either end of the tethered link 28 are configured to encourage two separate filaments to freely travel and move longitudinally throughout the tethered link 28. While there may be contact between two separate filaments threaded through the filament channel 62 of the tethered link 28, the divergent structure of the bifurcations 64, 66 towards the caps 68, 72 will limit tangling and frictional sticking between two filaments, allowing multiple filaments or sutures within the channel 62 to slide in a longitudinal direction while the occlusion device and its mobile link 26 and tethered link 28 are being placed, adjusted, and tightened.

FIG. 4B is a top perspective view of the second, bottom tethered link of FIG. 4A. FIG. 4B illustrates the respective locations of the filament apertures 80 of the cap 68, the filament apertures 76 of the beveled cap 72, as well as additional features from the top perspective of the tethered link 28. The top surface of the tethered link 28 defines a center protrusion 84, several ridges 86 on either side of the center protrusion 84, and several interstitial recesses 88 perpendicular to the center protrusion 84 and ridges 86. These features form a gripping surface resulting in opposing interdigitating surfaces on the tethered link 28 that correspond and interlock with similar features on the top surface of the upper mobile link. While the links shown in FIGS. 4A and 4B are substantially cylindrical, other embodiments of links may be more or less rounded, rectangular, tubular, or flat relative to the embodiment shown herein. FIGS. 5A, 5B, 5C, 5D, 5E, and 5F are front, left side, right side, rear, top, and bottom elevational views, respectively, of the bottom tethered link of FIGS. 4A and 4B. Alternate embodiments of a tethered link may have alternate lengths to accommodate anatomical variations or other sizing considerations related to left atrial appendages or other anatomical tissue structures.

The combination of the first mobile link, the second tethered link, and the configuration of the first link and the second link, each having filament channels along their respective longitudinal lengths, enables a compensating coupler in the occlusion device of the present disclosure. The compensating coupler can couple or connect the first link and the second link at either end or as in the embodiment shown, both ends. In this embodiment, the filament or suture, and the configuration of the internal filament channels and filament apertures at either end of each of the first link and the second link combine to establish the compensating coupler. While this compensating coupler is not a defined hinge or pivotable structure in the occlusion member—the structure formed by the two links may behave similarly to a hinge when the beveled ends of the first link and the second link are in close proximity when tightened or tensioned by the filament or suture threaded through each of the first link and second link.

Well-known hinged or spring-loaded occlusion devices may not fully compensate for a changing pressure gradient applied to tissue as the sides of an occlusion device close starting from a hinge side to an end side. Other well-known occlusion devices may close starting from a tip or end side to a hinge side while compressing tissue. Others close in parallel with fixed springs or rigid, fixed tensioned members forcing the closure of two beams or links together to complete a tissue occlusion.

The embodiments disclosed herein, having two independent beams fixed at one end or both ends by a compensating coupler, a coupler or connection or joint having a resilient, stretching, movable coupler of variable length allows the beams to occlude the longer outer base of a left atrial appendage or other tissue surfaces at a substantially parallel plane of closure rather than a triangular point of closure having an increasingly acute angle of closure at one end as compared to the other. In contrast to other devices that also close in a parallel plane of closure as forced closed by a spring or other rigid tensioning member, the occlusion device of the present disclosure provides a more consistent closure during which tension is applied manually, and the first link or the second link are allowed to pivot around anatomical variations in morphology of a left atrial appendage or other structure. An advantage is that the occlusion device disclosed herein may provide a more consistent closure pressure over the length of the base of the left atrial appendage or other anatomical feature to which the occlusion device is being applied. The freely moving filaments within the top link and the bottom link provide the closure with an operator controllable level of tension and slack as the occlusion device is applied and tightened or tensioned. The closure mechanism is simultaneous at both ends, thus pulling the parallel beams down with equal force. The occlusion device, however, is not strictly limited to parallel closure, nor does it exclusively close in a hinge-like, increasingly acute angled closure. The suture traveling through both beams allows for the dual compensating coupler joints to close with manually applied, near equivalent force toward the tissue and along the length of the link or beam. Encapsulation of the entire base of a left atrial appendage is insured by a combination of clamping pressure and ligation at the ends by the filaments or sutures. Other materials that are resilient or partially elastic filaments may also be used.

Figure 6A:
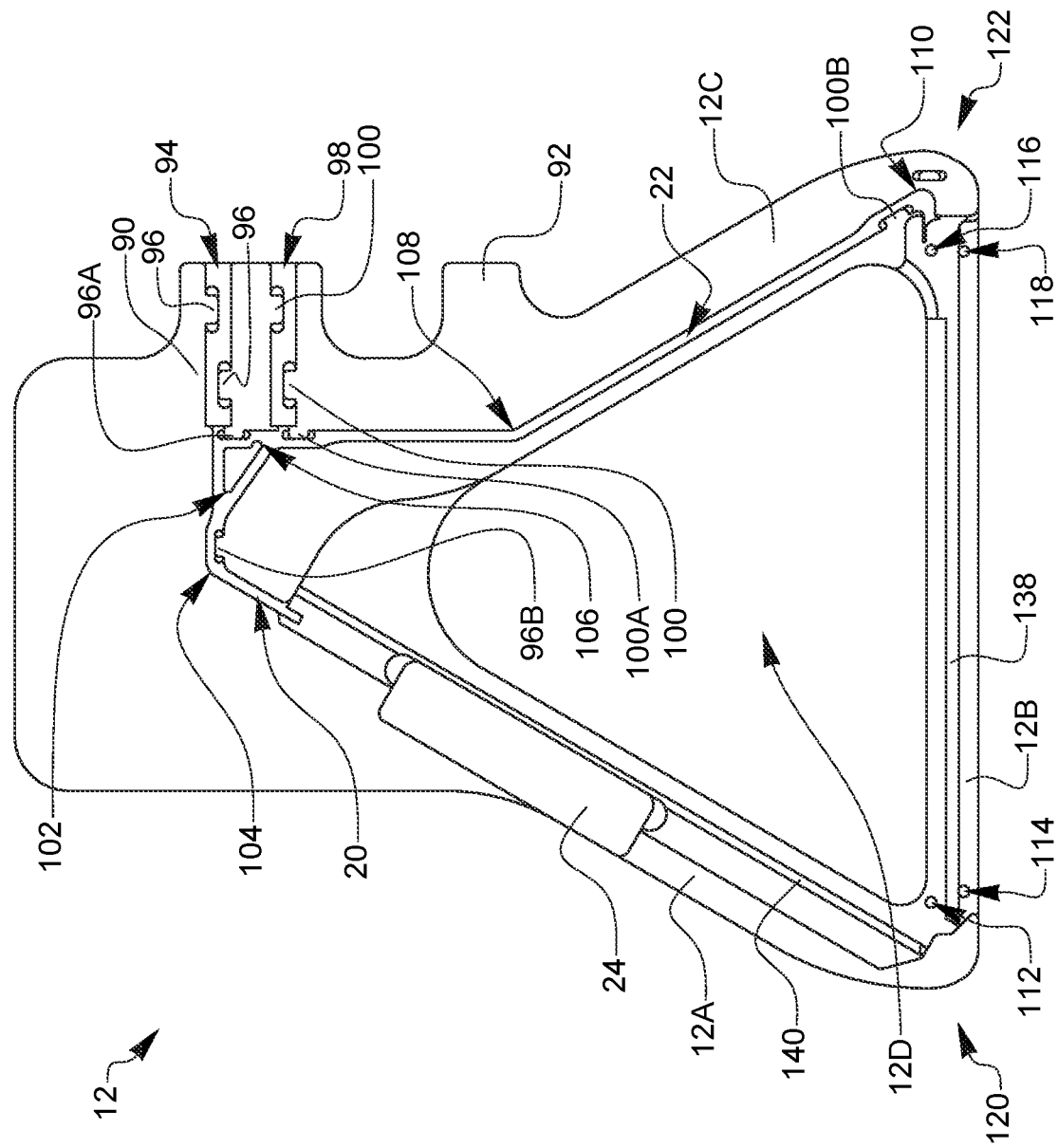

FIGS. 6A-6B are front and back views, respectively, of a delivery frame of the minimally invasive occlusion device of FIG. 1. FIG. 6A is a front view of the delivery frame 12 of the minimally invasive occlusion device 10 of FIG. 1. The delivery frame 12 defines a first extension 90, which further defines a first lumen recess 94 and a second lumen recess 98. The first lumen recess 94 is a partially cylindrical shaped recess suitable for releasably holding a tube or lumen. The first lumen recess 94 is bordered by two clips 96, configured to partially surround a tube inserted into the first lumen recess 94 and prevent an inserted tube or lumen from being removed prematurely. The second lumen recess 98 is also a partially cylindrical shaped recess suitable for releasably holding a tube or lumen. The second lumen recess 98 is bordered by two clips 100, configured to partially surround a tube inserted into the second lumen recess 98 and prevent an inserted tube or lumen from being removed unintentionally or prematurely. The first lumen recess 94 and the second lumen recess 98 are both in communication with the first filament channel 20 and the second filament channel 22. The first filament channel 20 branches off from the first lumen recess 94, its course including a first bend 102, a second bend 104, and down towards a side 12A of the triangular delivery frame 12 which holds the mobile link 26. In addition to the half cover or holder 24 on side 12A of the delivery frame 12 is a mobile link protrusion 140 that interfaces with beam recess 33 to align the placement of the first mobile link 26 which was described in regard to FIG. 2A into the delivery frame 12. The first filament channel 20 is also bordered by several filament clips 96A, 96B that aid in guiding and retaining threaded filament within the first filament channel 20.

The second filament channel 22 primarily branches off from the second lumen recess 98, its course including a first bend 106, a second bend 108, down towards a side 12C of the triangular delivery frame 12, around a third bend 110, and towards a side 12B of the delivery frame 12. The frame side 12B also defines a tethered link protrusion 138 that interfaces with beam recess 61 to align the placement of the second tethered link 28 which was described in regard to FIG. 2A into the delivery frame 12. The second filament channel 22 is also bordered by several filament clips 100A, 100B that aid in guiding and retaining threaded filament within the second filament channel 22. At one end of frame side 12B, adjacent to the corner 120 between frame side 12A and frame side 12B there are two apertures 112, 114. Also, at another end of frame side 12B, adjacent to the corner 122 between frame side 12B and frame side 12C, there are two additional apertures 116, 118. The three sides 12A, 12B, and 12C of the triangular delivery frame 12 also define an opening 12D.

FIG. 6B is a back view of the delivery frame 12 of the minimally invasive occlusion device 10 of FIG. 1. The first extension 90 and the second extension 92 of the delivery frame 12 are shown from the back side of the delivery frame 12. The second extension 92 defines a third lumen recess 124. The third lumen recess 124 is a partially cylindrical shaped recess suitable for releasably holding a tube or lumen. The third lumen recess 124 is bordered by two clips 126, configured to partially surround a tube inserted into the third lumen recess 124 and prevent an inserted tube or lumen from being removed unintentionally or prematurely. The third lumen recess 124 is in communication with the third filament channel 30. The third filament channel 30 branches off from the third lumen recess 124, its course including a first bend 128, a second bend 132, and down towards side 12C of the triangular delivery frame 12. The third filament channel 30 also defines a first relief passage 130 and a second relief passage 134 before and after the second bend 132, respectively at corner 122 between frame side 12C and frame side 12B. The first relief passage 130 and second relief passage 134 provide an increased area within the third filament channel 30 for allowing additional room for a filament placed in the third filament channel 30 an increased radius for being tightened around the second bend 132. The third filament channel 30 terminates in a bifurcation 136A, 136B the branches of which are in communication with aperture 116 and aperture 118 respectively. The locations of the apertures 112, 114 near the opposite corner 120 are also indicated in FIG. 6B. The use and purpose of the apertures 112, 114, 116, 118 and the third filament channel 30 will be discussed later.

Figure 7B:
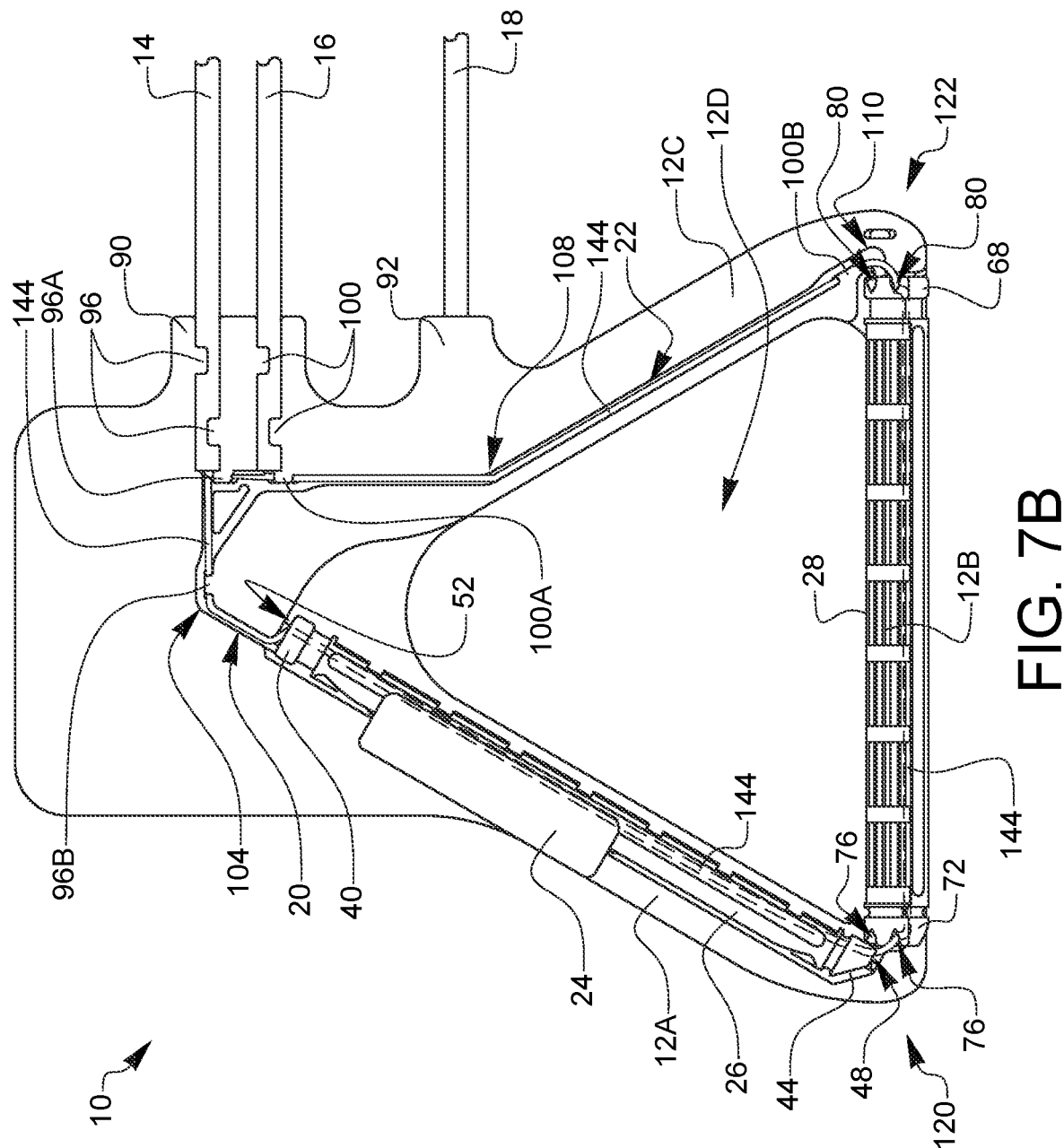
Figure 7C:
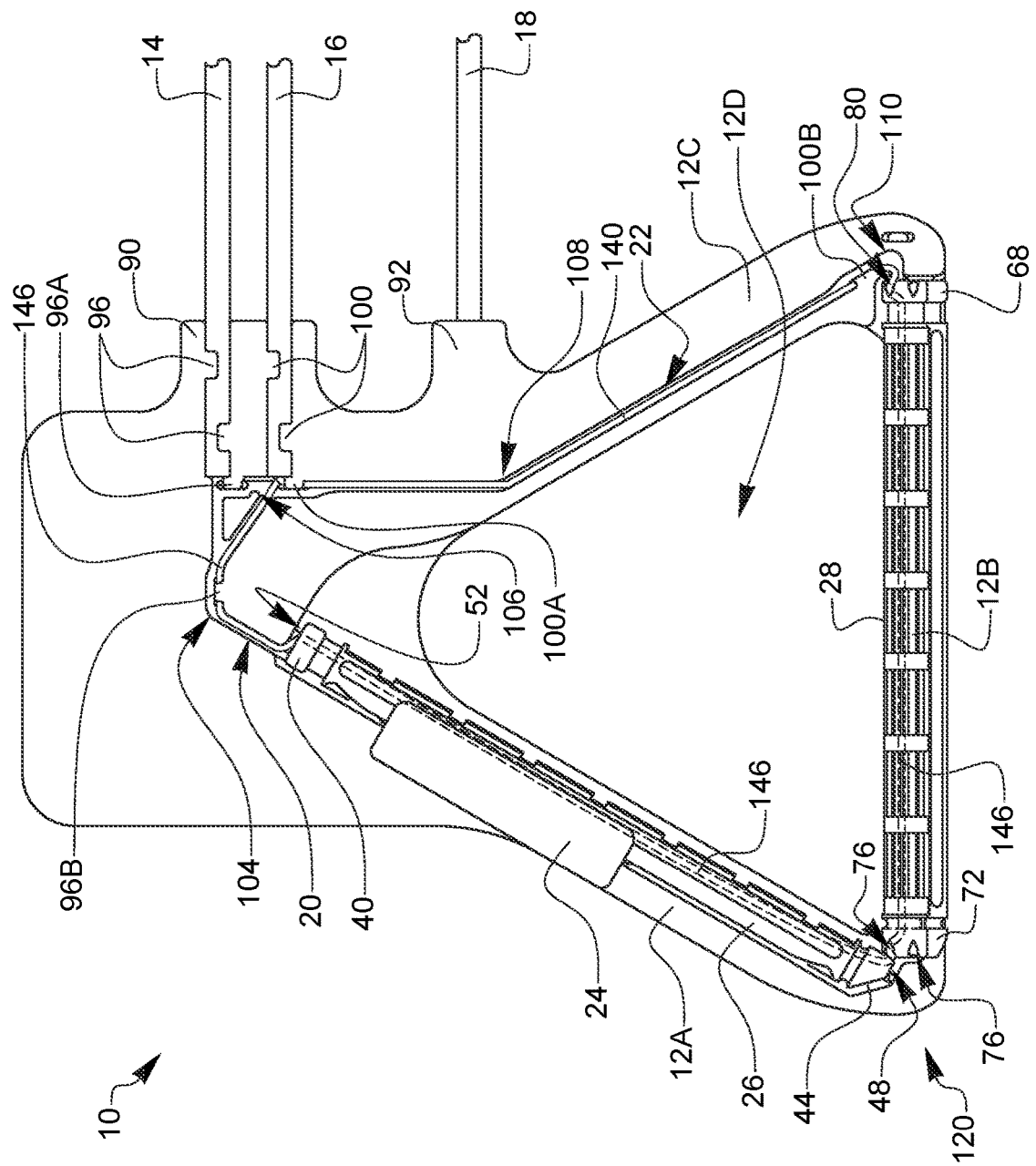

FIGS. 7A, 7B, and 7C are back, front, and front views, respectively, of the minimally invasive occlusion device of FIG. 1 illustrating various filament threading paths. FIG. 7A illustrates a filament threading path for retaining the tethered link 28 onto frame side 12B of the triangular delivery frame 12. Placed within the third lumen recess 124, which is not visible in this view, is a third filament lumen 18 held in place in the third lumen recess 124 by the two clips 126. A ripcord suture 142 exits the third filament lumen 18 and is threaded on a course around the first bend 128 in the third filament channel 30, down along frame side 12C, around second bend 132, along bifurcation 136A, into additional apertures 116, around circumferential recesses 78 on the caps 72 of tethered link 28, back through aperture 118 and along frame side 12B of the triangular delivery frame 12. As the ripcord suture 142 is threaded towards corner 120 along frame side 12B, the ripcord suture 142 is inserted into aperture 114, around circumferential recesses 70 on the caps 68 of tethered link 28. The ripcord suture 142 is then threaded back through aperture 112, along frame side 12B, into the bifurcation 136A, back around second bend 132 of third filament channel 30, around first bend 128 and back into the third filament lumen 18.

FIG. 7B illustrates a filament threading path for a first suture or filament that is used in the operation of the minimally invasive occlusion device of FIG. 1A. The first filament lumen 14 is placed within the first lumen recess 94 on the first extension 90 and held in place by two clips 96. A first suture 144 exits the first filament lumen 14 and enters the first filament channel 20, is threaded around the second bend 104 of the first filament channel 20 and into one of the two filament apertures 52 on cap 40 of the first mobile link 26. The suture is passed through the internal channel of the first mobile link 26, out of filament aperture 48 on the beveled cap 44, and directly into filament aperture 76 on the beveled cap 72 of the tethered link 28. The suture is passed through the internal channel of the tethered link 28 out from the filament aperture 80 of the cap 68 on the end of the tethered link 28. The first suture 144 is then passed around the third bend 110 of the second filament channel 22, under filament clip 100B, around the second bend 108 of the second filament channel 22, under filament clip 100A, under filament clip 96A, and finally back into the first filament lumen 14.

FIG. 7C illustrates a filament threading path for a second suture or filament that is used in the operation of the minimally invasive occlusion device of FIG. 1A. The second filament lumen 16 is placed within the second lumen recess 98 on the first extension 90 and held in place by two clips 100. A second suture 146 exits the second filament lumen 16 and enters the first filament channel 20, is threaded around the first bend 106 of first filament channel 20, followed by the second bend 104 of the first filament channel 20, under clip 96B and into one of the two filament apertures 52 on cap 40 of the first mobile link 26. The suture is passed through the internal channel of the first mobile link 26, out of another of the filament apertures 48 on the beveled cap 44, and directly into another filament aperture 76 on the beveled cap 72 of the tethered link 28. The suture is passed through the internal channel of the tethered link 28 out from one of the filament apertures 80 of cap 68 on the end of the tethered link 28. The second suture 146 is then passed around the third bend 110 of the second filament channel 22, under filament clip 100B, along frame side 12C, around the second bend 108 of the second filament channel 22, under filament clip 100A, and finally back into the second filament lumen 16.

Figure 8A:
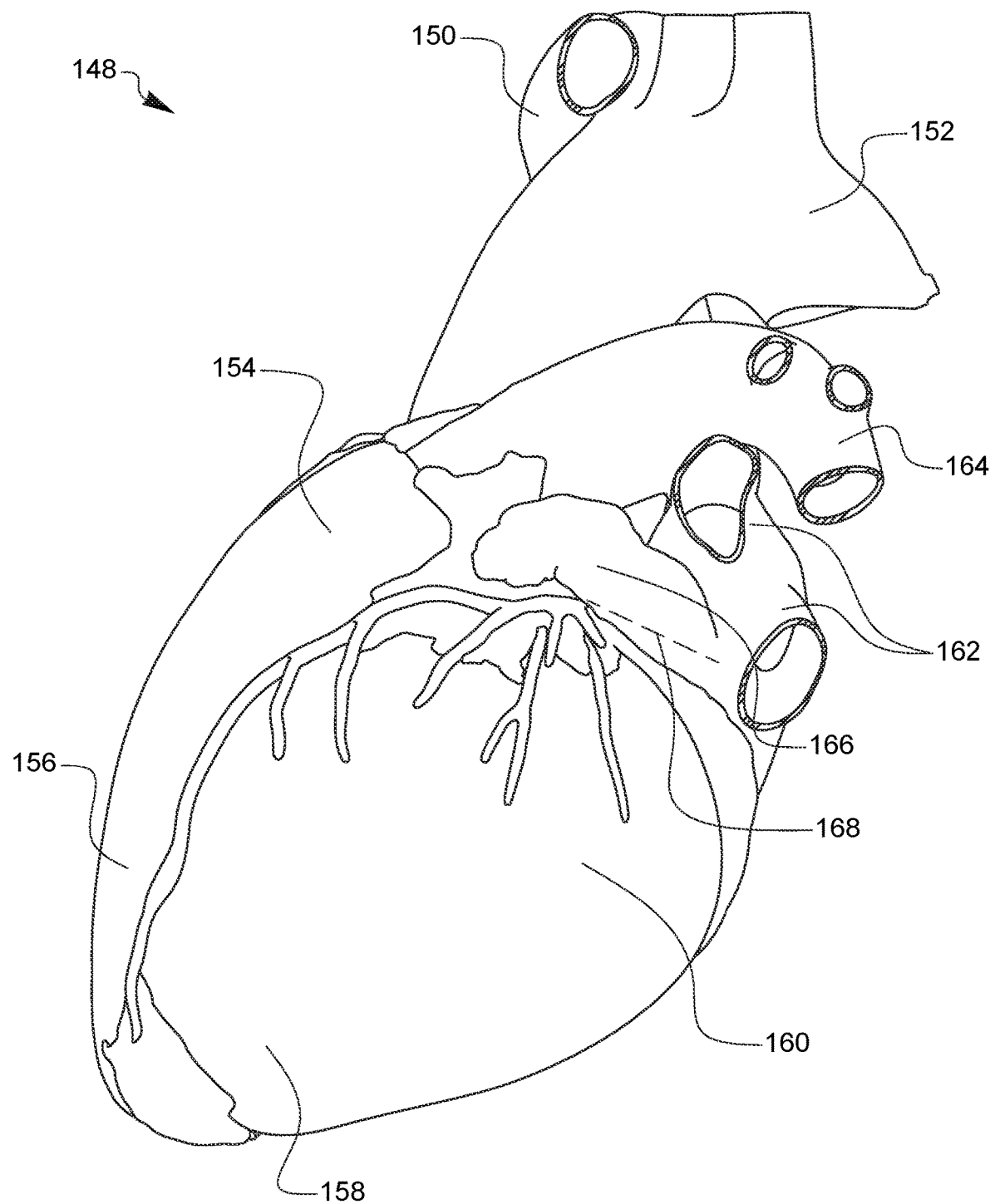
FIGS. 8A-8I are a series of perspective views illustrating a surgical sequence demonstrating the use of the minimally invasive occlusion device of FIG. 1.

FIGS. 8A-8I are a series of perspective views illustrating a surgical sequence demonstrating the use of the minimally invasive occlusion device of FIG. 1. FIG. 8A is a schematic illustration of a heart 148 showing several features and anatomical components of the heart 148 in context and in relation to a left atrial appendage 166 (LAA) and the base 168 of the left atrial appendage 166. The relative locations of the superior vena cava 150, the aorta 152, the pulmonary artery trunk 164, and pulmonary veins 162 are indicated in FIG. 8A. The locations of the right atrium 154, right ventricle 156, left ventricle 158, and the left atrium 160 are also indicated. In a surgical setting, the heart 148, either beating or arrested, would be exposed or accessible via median sternotomy or hemisternotomy, with a surgeon accessing the surgical site from a patient's right side.

Figure 8B:
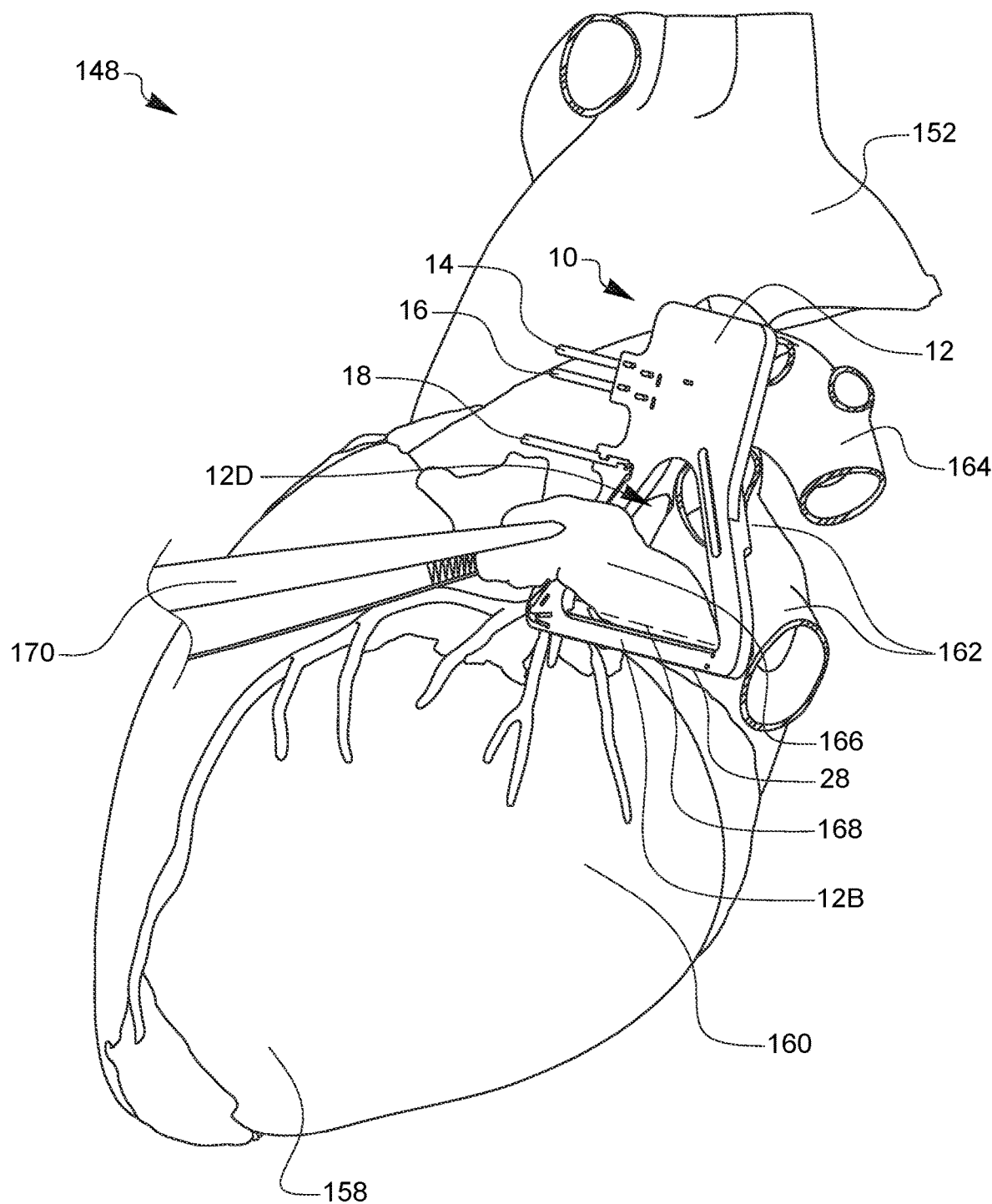
Figure 8C:
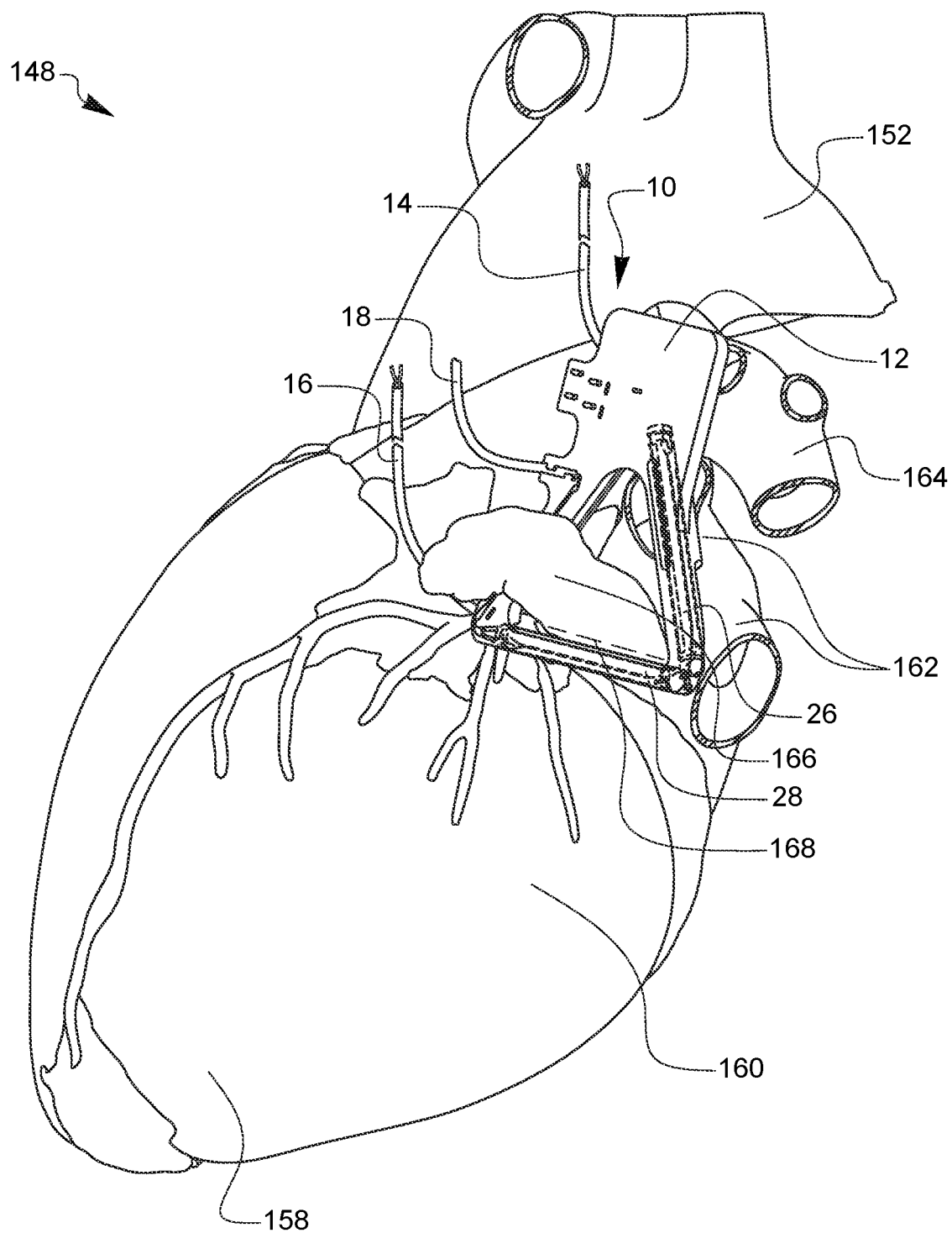

FIG. 8B illustrates the placement of a minimally invasive occlusion device 10 laterally with frame side 12B of the delivery frame 12 positioned lateral to the left atrial appendage 166 at its base 168, avoiding contact with the pulmonary artery trunk 164 and pulmonary veins 162. The first filament lumen 14, second filament lumen 16, and third filament lumen 18 are shown cross-sectioned in this view, but they are extended outside of the surgical site with the lumens 14, 16, 18 or tubes generally facing caudad. Using the assistance of graspers 170, the left atrial appendage 166 is pulled through the opening 12D in the delivery frame 12 of the minimally invasive occlusion device 10. Using grasper or fingers, the body of the LAA 166 is pulled up thru the opening 12D in the delivery frame 12 while avoiding squeezing or "milking" a potential blood clot from the LAA 166 pocket or its mural attachment. During this step, the surgeon should also avoid enclosing or clamping circumflex artery or coronary venous structures. FIG. 8C shows the positioning of the tethered link 28 parallel to the long axis or base 168 of the LAA 166 and the released state of the first filament lumen 14 and the second filament lumen 16 from their respective lumen recesses in the delivery frame 12 of the minimally invasive occlusion device 10. The ends of the first suture 144 and the second suture 146 exit the ends of the first filament lumen 14 and the second filament lumen 16, respectively. These sutures 144, 146 may be secured externally to the patient using clamps, suture locking devices, or other means known to those skilled in the art.

Figure 8D:
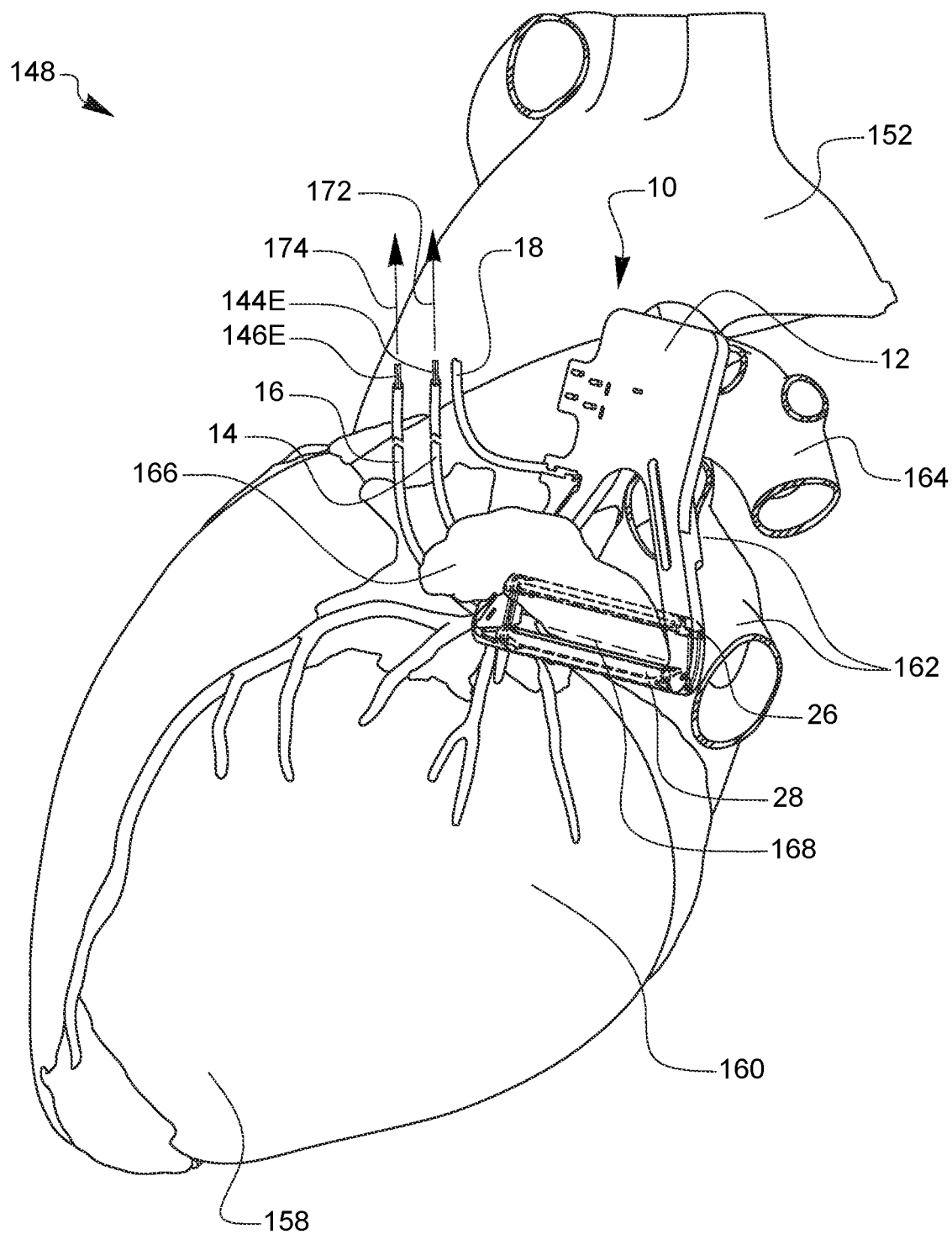
Figure 8E:
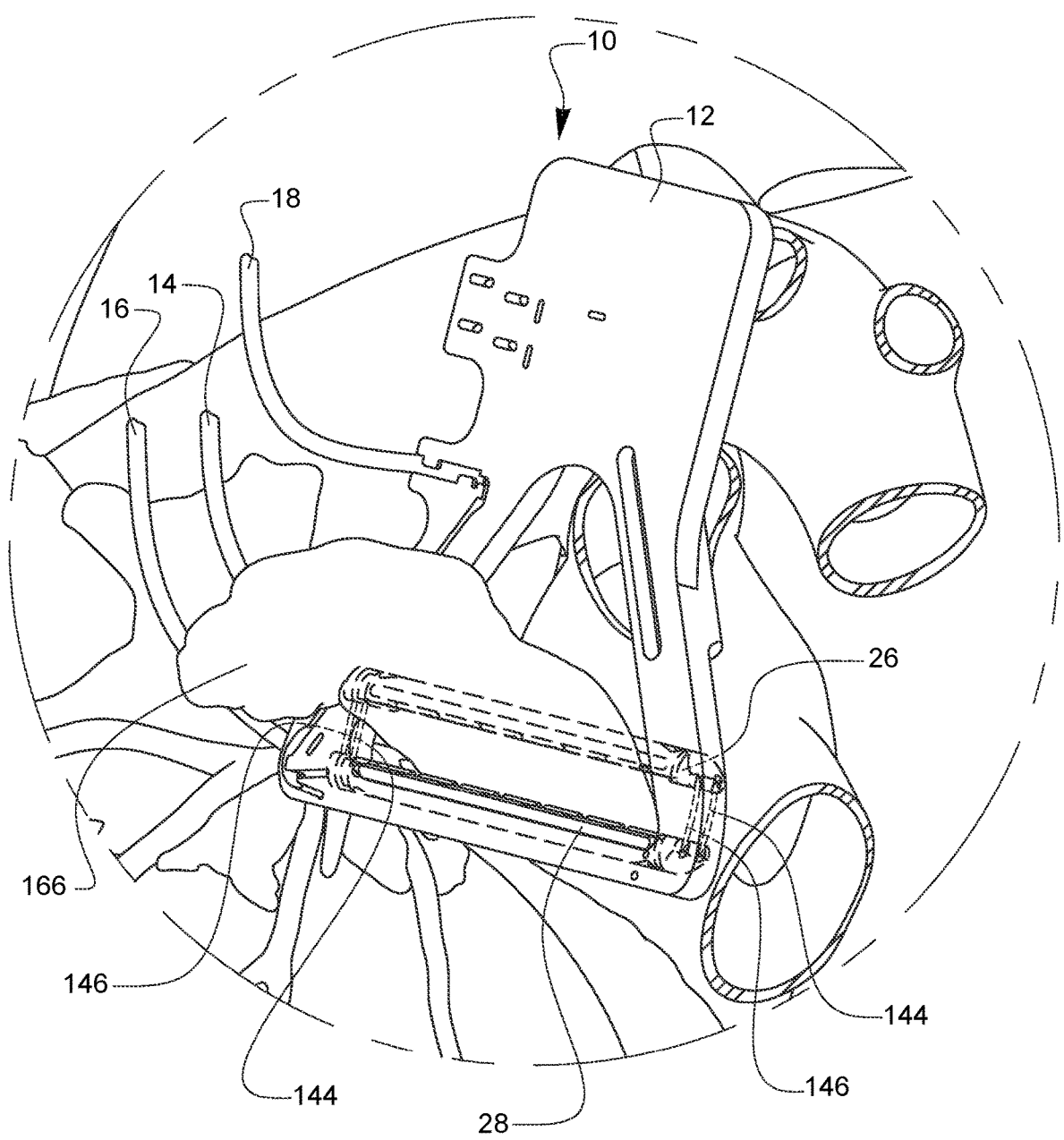

FIG. 8D illustrates the first mobile link 26 of the minimally invasive occlusion device 10 released from its holder in the delivery frame 12 and rotated approximately 45 degrees to a substantially parallel position relative to the tethered link 28. In this position the first mobile link 26 and the tethered link 28 are also substantially parallel to the base 168 of the left atrial appendage 166. The ends 144E of the first suture 144 and the ends 146E of the second suture 146 are pulled in direction 172 and in direction 174, respectively, to take up any slack in the sutures 144, 146. It should be noted that subsequent tightening or tensioning of the sutures 144, 146 will be accomplished by pulling in these same directions 172, 174. Before tightening the sutures 144, 146 fingers, forceps or graspers may be used to more appropriately position the first mobile link 26 along the more medial side of the left atrial appendage 166 while encircling the entire base 168 structure of the left atrial appendage 166 with either the first mobile link 26, tethered link 28, or the sutures 144, 146. At this point, both sutures 144, 146 can be pulled through their respective lumen 14, 16 or tube to fully tighten the first mobile link 26 and the tethered link 28 around the left atrial appendage 166 to accomplish complete occlusion. While the tightening of one suture should be adequate to sufficiently close the links 26, 28 together, the use of a second suture provides additional security, as well as a second tensioning member to secure the occlusion device during a later step to finally secure the occlusion device with one or more mechanical fasteners. It should be noted that while the sutures may be tightened at this point, the clamps on the sutures may be reversibly secured, and any repositioning of the minimally invasive occlusion device 10 may still be done if under direct visual inspection or instrument visualization, echosonography for example, the surgeon determines repositioning is warranted. The previously described compensating coupler concept achieved by the configuration of the first mobile link 26, tethered link 28 and the slidable sutures 144, 146 which freely move within the internal filament channels in the first mobile link 26 and tethered link 28 allow for the minimally invasive occlusion device 10 to adjust as the sutures are tightened, accommodating for any anatomical variations in the left atrial appendage 166 that may be present from patient to patient. This state of the minimally invasive occlusion device 10 is illustrated in the enlarged view shown in FIG. 8E.

Figure 8F:
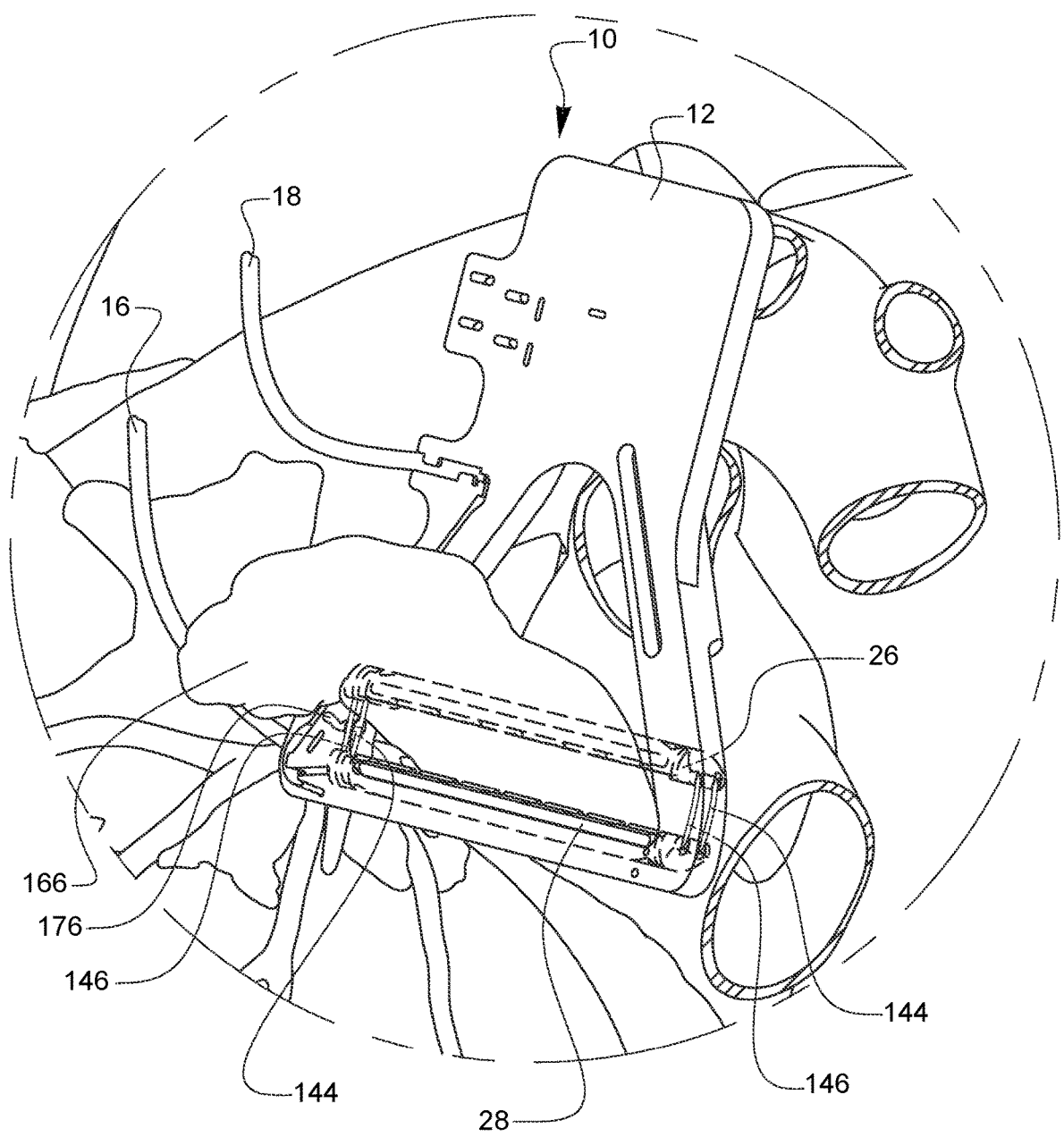
Figure 8G:
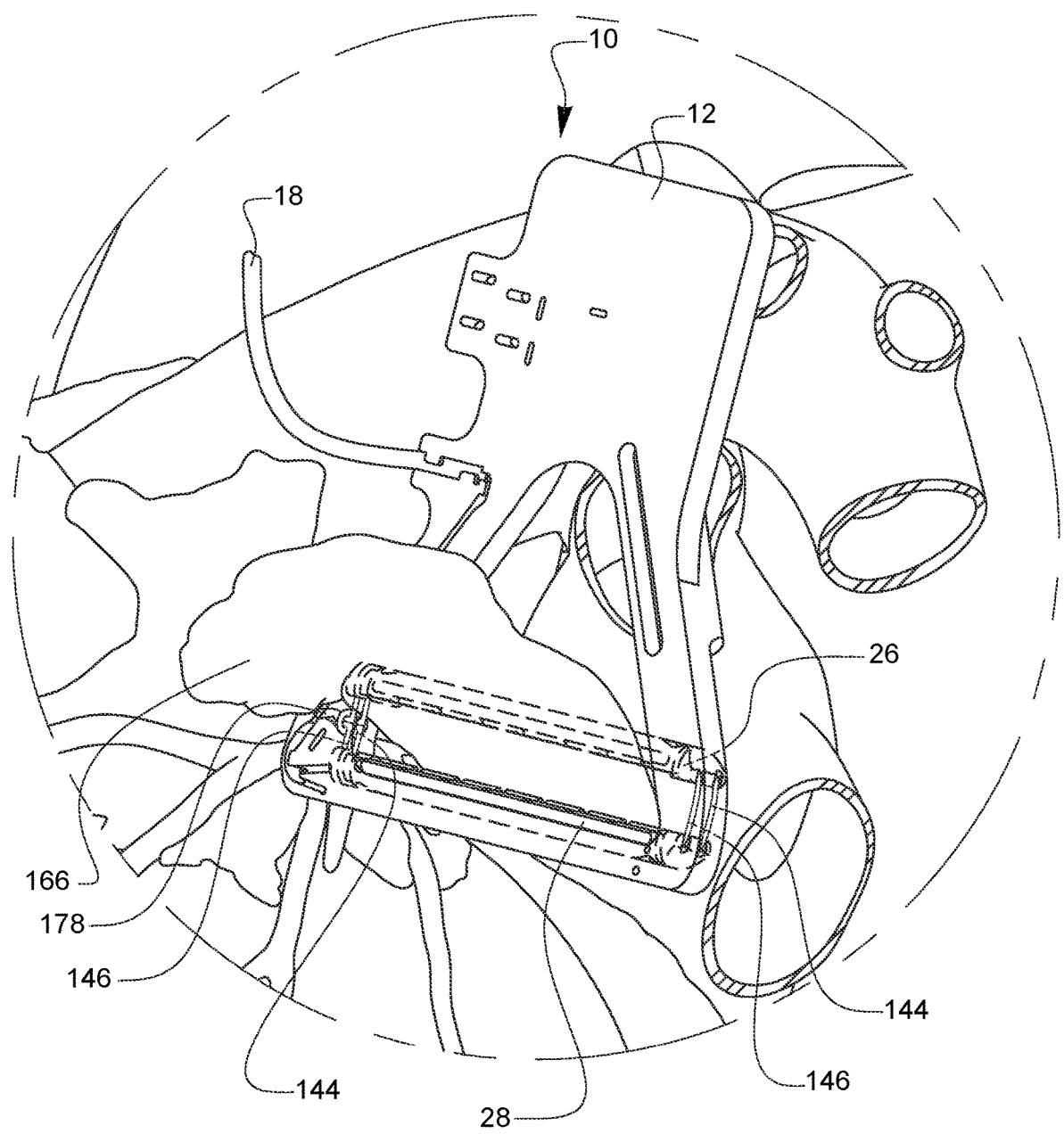

FIG. 8F is an enlarged view of the surgical site illustrated in FIG. 8A-8E. Once the position and placement of and tension upon the occlusion device is sufficient, the first filament lumen 14 can be removed, the suture ends snared within a mechanical fastener device (not shown but known to those skilled in the art), and a first mechanical fastener 176 is applied to the first suture 144, fully securing the minimally invasive occlusion device 10 around the left atrial appendage 166. While a first mechanical fastener 176 is used, a hand tied knot may also be used, although it is not recommended. FIG. 8G is an enlarged view of the surgical site illustrated previously. Once the first mechanical fastener 176 has been applied to the minimally invasive occlusion device 10 the second filament lumen 16 can be removed, the suture ends snared within a mechanical fastener device (not shown but known to those skilled in the art), and a second mechanical fastener 178 is applied to the second suture 146, doubly securing the minimally invasive occlusion device 10 around the left atrial appendage 166. While a second mechanical fastener 178 is used, a hand tied knot may also be used, although it is not recommended.

Figure 8H:
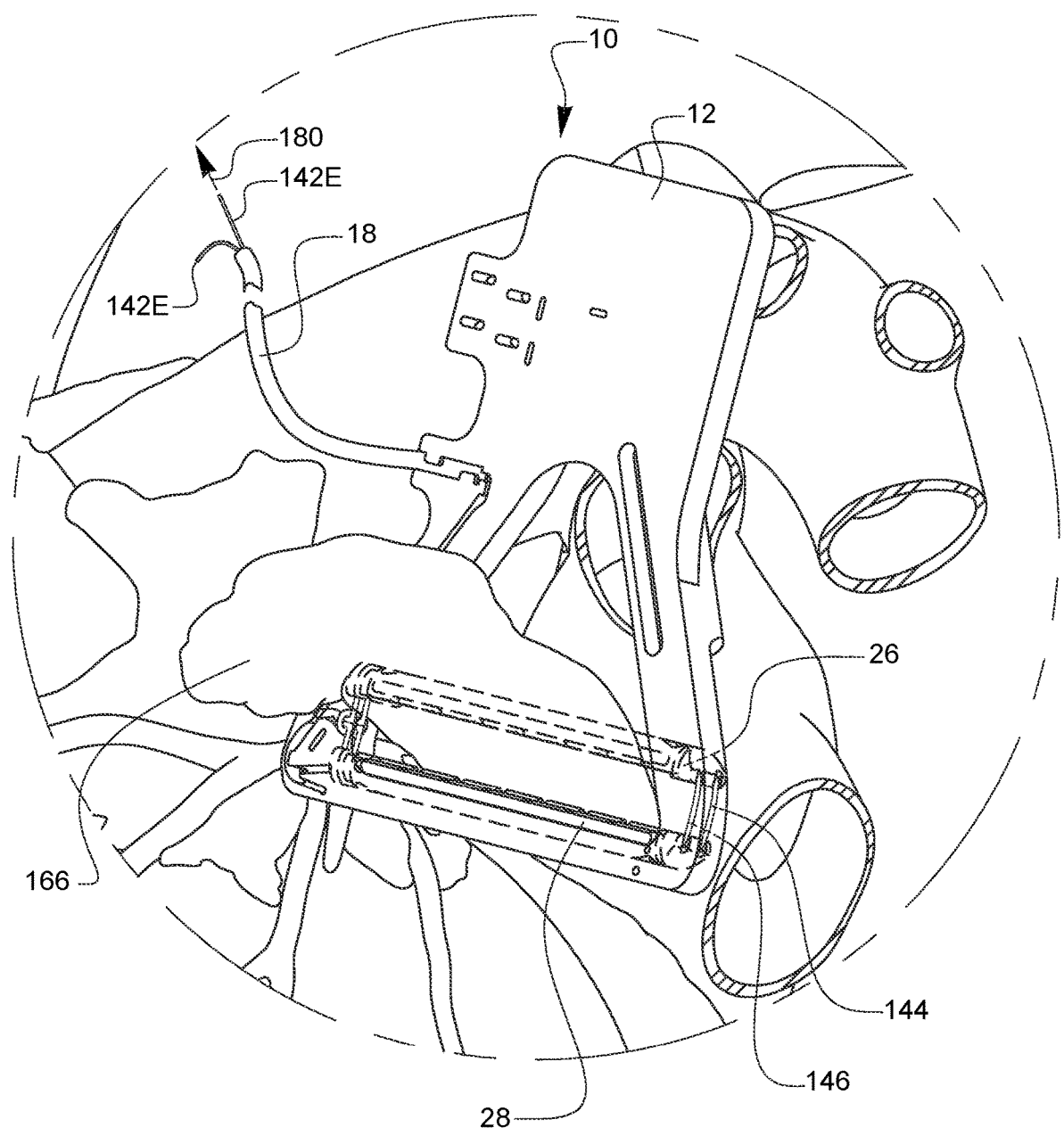
Figure 8I:
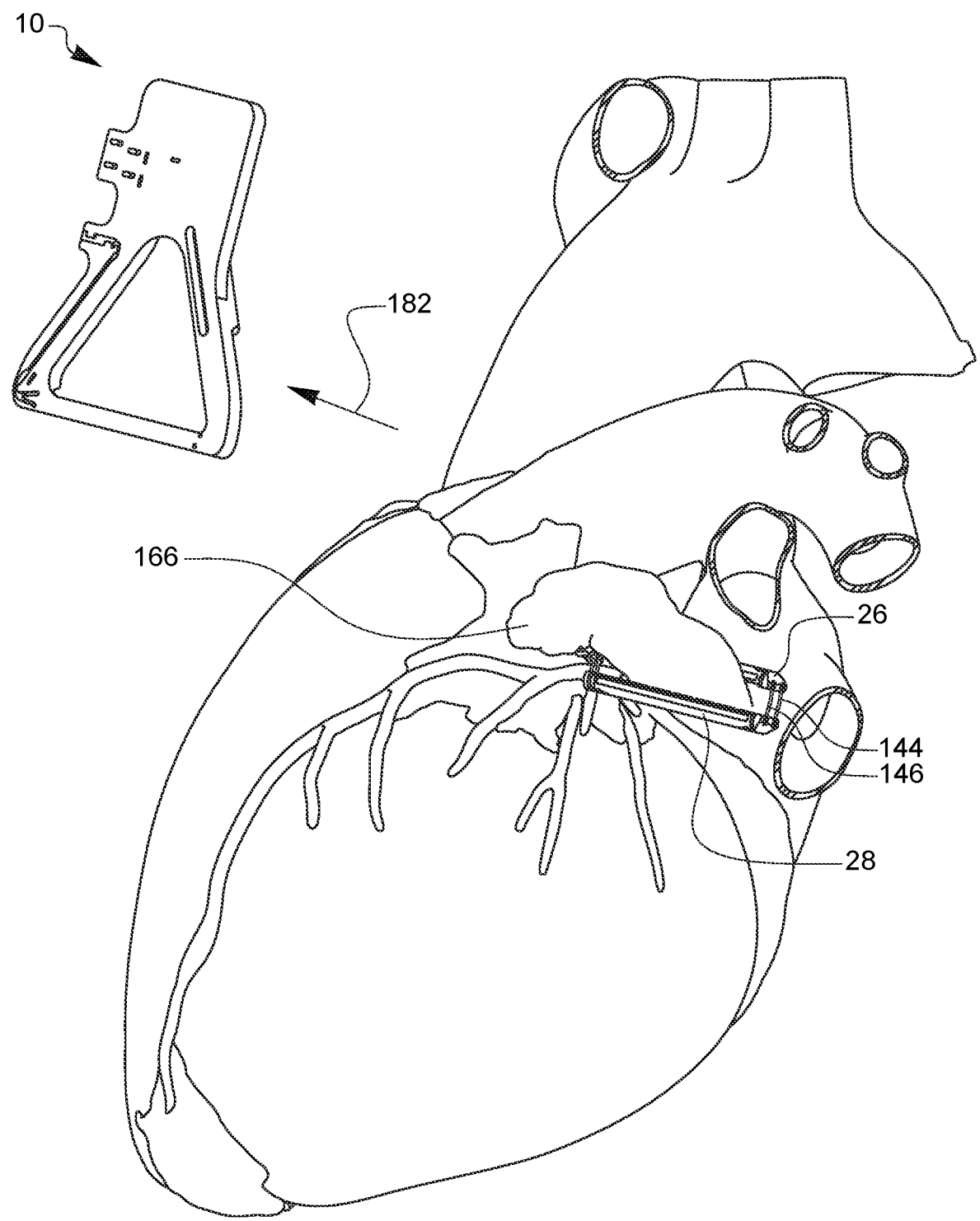

FIG. 8H is an enlarged view illustrating the state of the minimally invasive occlusion device 10 after the removal of ripcord suture 142 by pulling one of the ends 142E of the ripcord suture 142 in direction 180. The other end will advance through the threading within the occlusion device and exit from the third filament lumen 18. The ripcord suture 142 or tether suture has been removed and is no longer tethering the tethered link 28 to frame side 12B of the delivery frame 12. Then, the third filament lumen 18 may be removed from the delivery frame 12 of the minimally invasive occlusion device 10. FIG. 8I illustrates the removal of delivery frame 12 from the left atrial appendage 166 and from the surgical field in direction 182. It should be noted that the steps shown in FIGS. 8G, 8H, and 8I may be performed in different order at the discretion of the surgeon once the minimally invasive occlusion device 10 is secured to the base 168 of the left atrial appendage 166.

Figure 9:
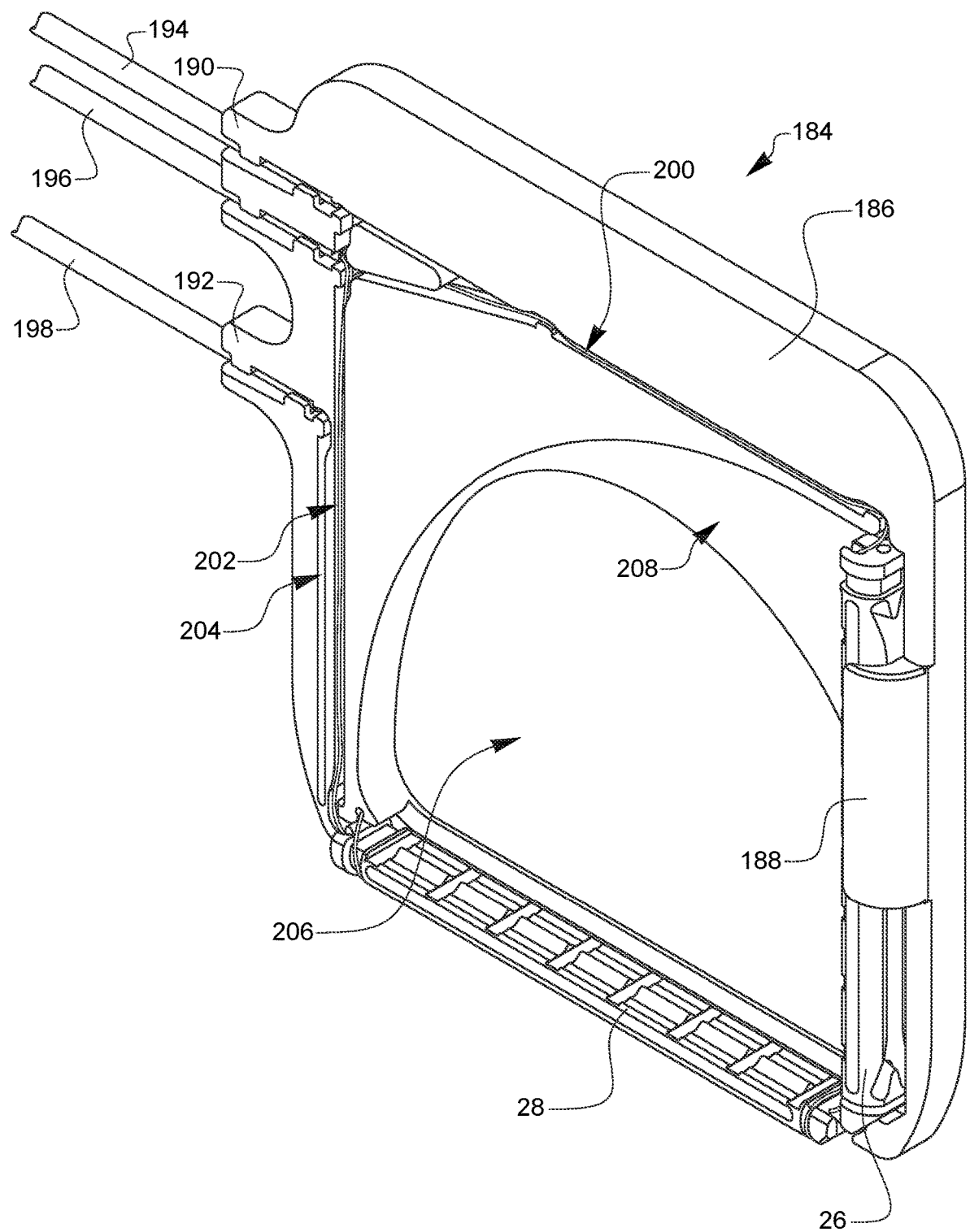
FIG. 9 is a perspective view of another embodiment of a minimally invasive occlusion device.

FIG. 9 is a perspective view of another embodiment of a minimally invasive occlusion device. The minimally invasive occlusion device 184 includes a square-shaped delivery frame 186 which is molded from a plastic translucent material. The delivery frame 186 defines a half cover or holder 188 which releasably holds a first mobile link 26, a first filament channel 200, and a second filament channel 202. A second tethered link 28 is also held to the frame 186 by a suture, which is not visible here. A first filament lumen 194, a second filament lumen 196 and a third filament lumen 198 are also held in the delivery frame 186 of the minimally invasive occlusion device 184. The first filament channel 200 and the second filament channel 202 are defined by the delivery frame 186 and are configured to hold and guide a filament, suture, or wire through the delivery frame 186 and through the mobile link 26 and the tethered link 28 until the minimally invasive occlusion device 184 is deployed. The delivery frame 186 also defines a third filament channel 204. This third filament channel 204 is also configured to hold and guide a filament, suture, or wire through the delivery frame 186 and around the tethered link 28 until the minimally invasive occlusion device 10 is deployed. An opening 206 in the delivery frame 186 for pulling a left atrial appendage or other tissue structure through the frame for occlusion is also present. This embodiment of a minimally invasive occlusion device 184 also has an arcuate closing guide 208 defined by the frame 186. This has the purpose of helping the operator guide a controlled closure of the first mobile link 26 onto the tethered link 28 during use. The operation and deployment of this embodiment of a minimally invasive occlusion device 184 is similar to previously described embodiments.

Figure 10A:
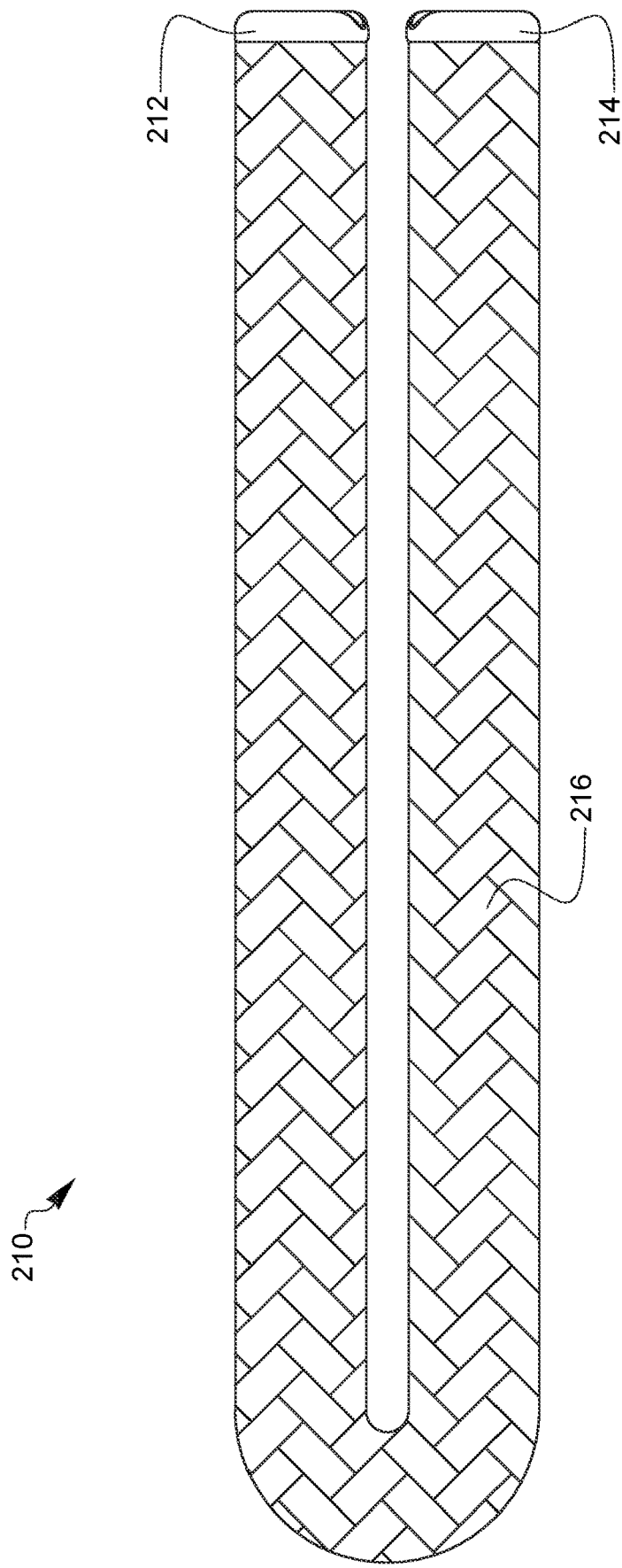
FIGS. 10A-10B are perspective views of alternate embodiments of links for use in a minimally invasive occlusion device.
Figure 10B:
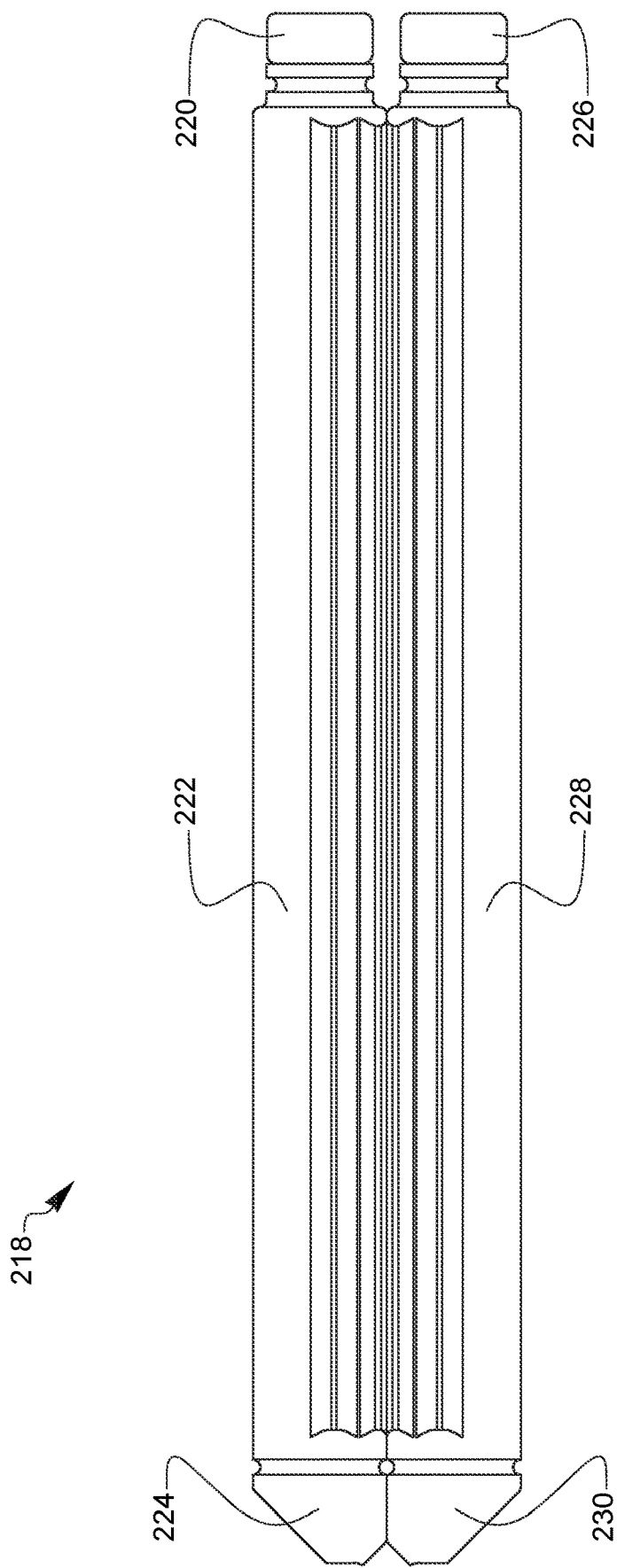

FIGS. 10A-10B are perspective views of alternate embodiments of links for use in a minimally invasive occlusion device. The alternate embodiment of a set of links 210 is illustrated in FIG. 10A in a closed position, indicating the locations of an end cap of first link 212 and the end cap of the second link 214. This embodiment is shown with a woven fabric cover 216 encapsulating both links. The woven cover may be constructed of polymer fibers such as polyethylene terephthalate, polyethylene glycol, caprolactone, and the like. The polymer fiber cover may be in the form of mesh, monofilaments, multifilaments, braids, and other applicable polymer fiber configurations. These types of covers or sheaths can help improve healing by encouraging sealing of occlusion devices and other medical occlusions similar to those described herein. FIG. 10B illustrates another alternate embodiment of a set of links 218, also shown in a closed position, indicating the locations of a first link end cap 220, a first link sheath 222, a first link beveled end cap 224, a second link end cap 226, a second link sheath 228, and a second link beveled end cap 230. The sheaths 222, 228 may be made of a variety of polymeric materials suitable for encouraging and supporting healing over an occlusion device, similar to the composition and function of the woven covers described in regard to FIG. 10B.

While some embodiments of delivery frames have been described herein, other delivery devices for delivering links and devices for occlusions such as those described herein may be used. For example, delivery devices including handles, shafts, mechanisms for releasing, and various distal tips useful in the introduction of occlusion devices may be used. One example of a suitable distal tip for such a delivery device may include an articulating cradle coupled to the shaft. Another example of a distal tip for such a delivery device may include a first jaw, a second jaw, and means for articulating these jaws for the purpose of effectively and accurately delivering an occlusion device to an intended surgical field area.

Figure 11:
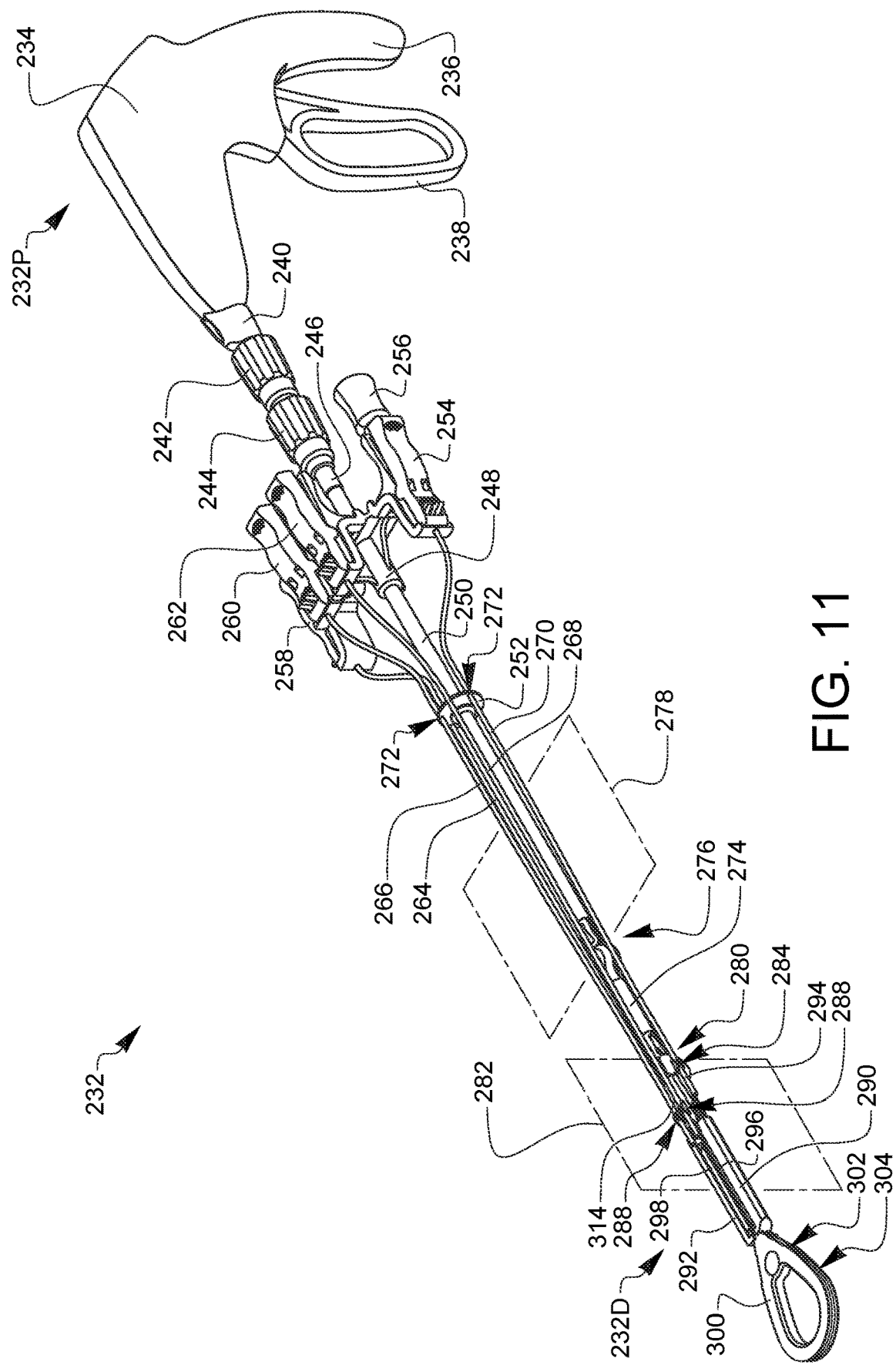
FIG. 11 is a top-left-front perspective view of an alternate embodiment of a delivery device for a minimally invasive occlusion device.

FIG. 11 is a top-left-front perspective view of an alternate embodiment of a delivery device for a minimally invasive occlusion device. A delivery device 232, alternatively an introducer device, having a housing 234, a handle 236, and an, actuator lever 238 at its proximal end 232P also has a rotation adapter 240, a first articulation knob 242, and a second articulation knob 244. The rotation adapter 240 serves to rotate the entire distal end 232D of the delivery device 232 about an axis of a shaft 250, which is connected to the housing 234 at the end of the second articulation knob 244. The rotation adapter 240, first articulation knob 242, and second articulation knob 244 are attached to the housing 234 using a retainer 246. The retainer 246 may be fixedly attached to the shaft 250 via adhesives, welding, or other means known to those skilled in the art. Also mounted onto the shaft is a suture lock mount 248 which is configured to hold two side suture locks 254, 258 and two top suture locks 260, 262. These suture locks 254, 258, 260, 262 are configured to retain and releasably lock sutures passed therethrough. Visible in one side suture lock 254 is a pull tab 256 which can be attached to the proximal end of a suture and utilized to pull the suture in a proximal direction during a procedure using such a suture lock 254. While only one pull tab 256 is visible here, one may or may not be a part of each of the suture locks 254, 258, 260, 262 in alternate embodiments. Protruding from each suture lock 254, 258, 260, 262 is a suture tube 270, 268, 264, 266, respectively, which holds within it a suture or other suitable filament. These suture tubes 270, 268, 264, 266 further aid in keeping sutures organized during the use of such a delivery device 232 and its related minimally invasive surgical procedures. Along the shaft 250 is a suture tube guide 252 which defines several notches 272 around its circumference. These notches 272 will releasably hold several suture tubes 270, 268, 264, 266 in place close to the shaft 250 prior to use of the delivery device 232. Further towards the distal end 232D of the delivery device 232 is a first articulation joint 276 which can be moved about a first plane of articulation 278 by actuating the first articulation knob 242. Connected to the first articulation joint 276 is a secondary shaft 274 which is then connected to a second articulation joint 280. This second articulation joint 280 can be moved about a second plane of articulation 282 by actuating the second articulation knob 244. The second articulation joint 280 is defined by a distal housing 314 which further defines a side suture tube guide 284 on either side and two top suture tube guides 288. These suture tube guides 284, 286, 288 releasably hold the suture tubes in place close to the distal housing 314, where the sutures exit the suture tubes 270, 268, 264, 266. Also attached to the distal housing 314 are two articulating jaws, a first jaw 290 which holds a first link 296 and a second jaw 292 which holds a second link 298. At the end of the first jaw 290 and the second jaw 292 is a suture target 300 that defines a first suture groove 302 and a second suture groove 304, which each hold a suture in place until the delivery device 232 is in use. Two sutures, which are not visible in this view, are held in the top suture locks 260, 262, in their respective suture tubes 264, 268, and exit the suture tubes 264, 268 to lash or anchor the first link 296 to the first jaw 290 and the second link 298 to the second jaw 292.

Two sutures, which are not visible in this view, are held in the side suture locks 254, 258, in their respective suture tubes 270, 266, and exit the suture tubes 270, 266 to be threaded through the first link 296 and the second link 298 and then through the suture target 300. The threading through and attachment onto the left atrial appendage for occlusion utilizing the links 296, 298 in this delivery device 232 is similar to the threading described in previous embodiments described herein. The delivery device 232 is used to introduce the links 296, 298 around the base of left atrial appendage rather than the previously described card or frame delivery device. This elongated articulating jaw embodiment of a left atrial appendage occlusion delivery device 232 allows for introduction into a less invasive space than a full sternotomy, for example, via a sub-xiphoid introduction or a right lateral mini thoracotomy. It should further be noted that the delivery device 232 is arranged and configured such that the links 296, 298 are loaded into the jaws 290, 292 face to face, resulting in a closed position relative to one another. Upon deployment and use of the delivery device 232, the links 296, 298 are first opened, then pivoted towards each other, such that the positional angle between the links 296, 298 becomes more acute until closure around tissue such as the left atrial appendage provides some resistance. At this time, the links may be released from the jaws 290, 292 and the compensating coupler mechanism allows for the folded portion or joined portion of the two links 296, 298 to accommodate a variety of anatomical variations and sizes of tissue structures being occluded. This feature provides a parallel, near parallel, or substantially parallel closure of the two links 296, 298 around a left atrial appendage or other tissue structure when tightened by a filament or suture independent of the delivery device 232.

Figure 12:
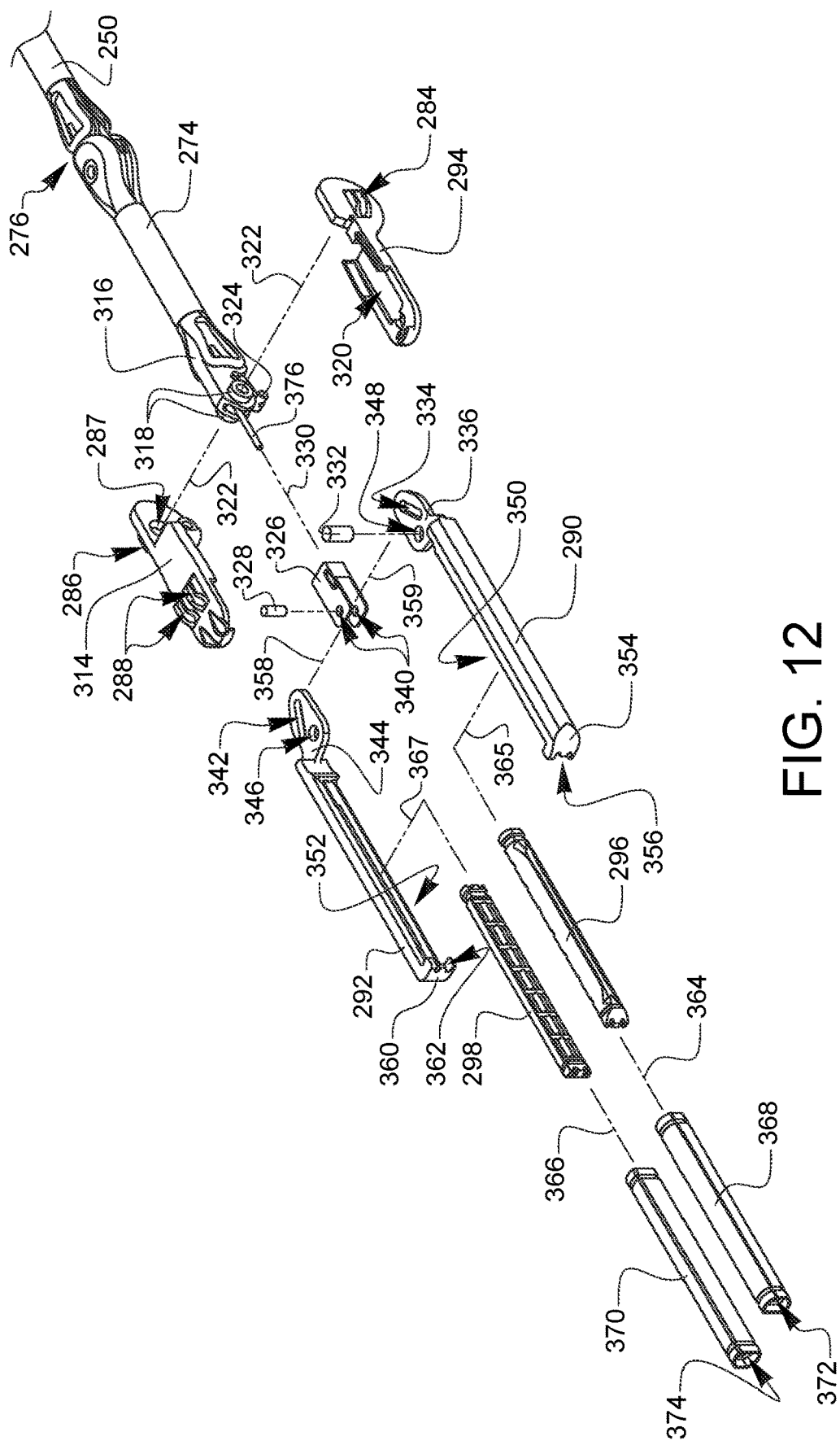
FIG. 12 is an exploded view illustrating the assembly of the distal tip of the delivery device of FIG. 11.

FIG. 12 is an exploded view illustrating the assembly of the distal tip of the delivery device of FIG. 11. At the end of the shaft 250 and the first articulation joint 276 is a secondary shaft 274. The secondary shaft 274 has a hinge 316 defining two axles 318 at its end and has a second articulation control rod 324 protruding distally. Also protruding distally is a pusher rod 376. A distal housing cover 294 is placed onto an axle 318 along axis 322. The distal housing cover 294 defines an internal recess 320. This recess 320 is shaped and configured to receive a pusher 326, which is placed onto the pusher rod 376 along axis 330 and is able to slide distally and proximally inside the recess 320 of the distal housing cover 294. A first jaw 290 defining a jaw hinge 336 having a slot 334 and a pivot hole 348 is placed inside the pusher 326 along axis 359. The first jaw 290 also defines a jaw recess 350, a jaw end 354, and a suture recess 356 in the jaw end 354. A second jaw 292 defining a jaw hinge 344 having a slot 342 and a pivot hole 346 is placed inside the pusher 326 along axis 358. The second jaw 292 also defines a jaw recess 352, a jaw end 360, and a suture recess 362 in the jaw end 360. Once the pusher 326 is placed onto the pusher rod 376, and the jaws 209, 292 are placed into the pusher 326, a pin 328 is placed through a top hole 340 defined by the pusher 326, through slot 342 of second jaw 292, through slot 334 of first jaw 290 and fixedly attached to the end of the pusher rod 376. The jaws 290, 292 are assembled by placing pivot pin 332 through hole 346 on the second jaw 292 and through hole 348 on the first jaw 290. The distal housing 314 is then placed onto axle 318 of hinge 316 and onto distal housing cover 294 holding the pusher 326, pin 332, and jaw hinge 344 and jaw hinge 336 captive within the distal housing. As the pusher rod 376 is moved proximally by squeezing the actuation lever of the delivery device, the jaws 290, 292 will move from an open to a closed position. This will be described later in further detail. Sheath 368 is placed onto first link 296 by inserting first link 296 into the center 372 of sheath 368 along axis 364. Sheath 370 is placed onto second link 298 by inserting second link 298 into the center 374 of sheath 370 along axis 366. Link 296 is placed into jaw recess 350 of first jaw 290 along axis 365, and link 298 is placed into jaw recess 352 of second jaw 292 along axis 367, completing the assembly of the delivery device. The links 296, 298 are then secured to the jaws 290, 292 with the use of the aforementioned sutures.

Figure 13A:
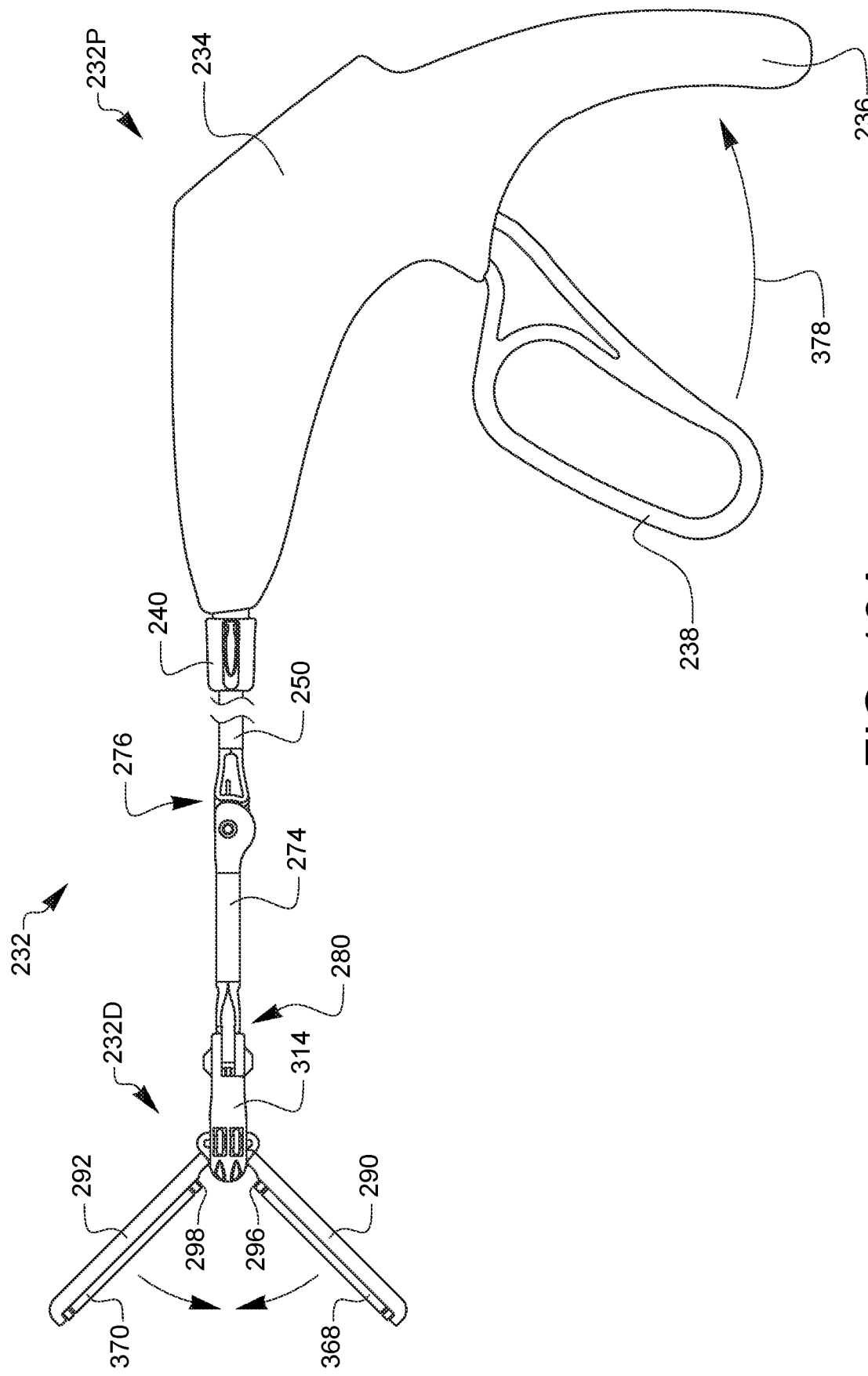
FIGS. 13A and 13B are side views illustrating the operational principles of the delivery device of FIG. 11.
Figure 13B:
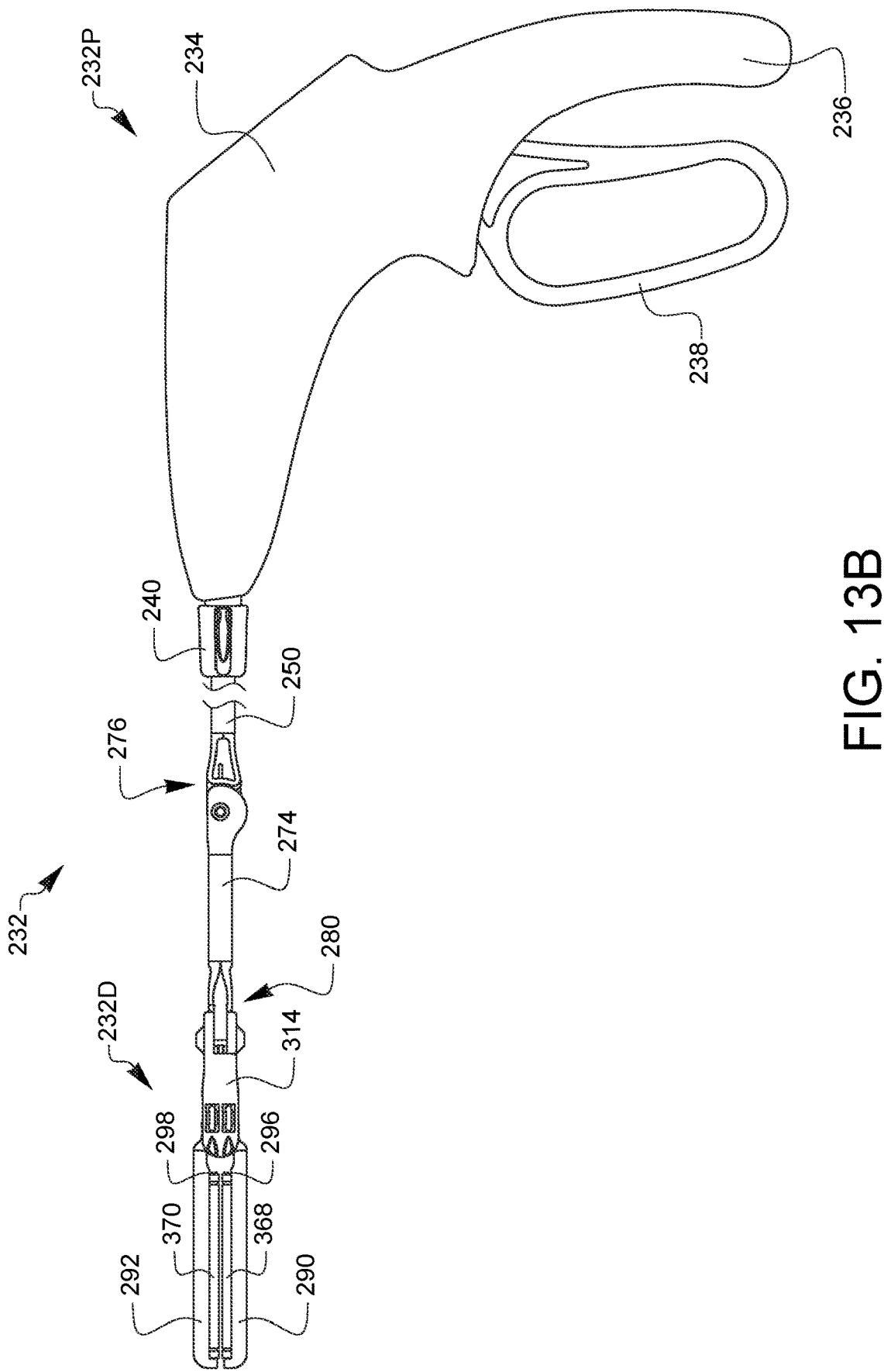

FIGS. 13A and 13B are side views illustrating the operational principles of the delivery device of FIG. 11. In a minimally invasive surgical procedure for occlusion of the left atrial appendage, the delivery device 232 is used to deliver an occlusion to the base of the left atrial appendage (LAA). Using sub-xiphoid access to the beating or arrested heart and great vessels with surgeon on patient's right side, the left atrial appendage is exposed. The target 300 is removed and the suture loops held therein are passed around the left atrial appendage with the assistance of a grasper or other surgical instrument capable of holding or grasping the left atrial appendage. The delivery device 232 is passed towards the left atrial appendage along the suture loops using a Seldinger-like technique. Near the LAA, the suture locks are released, and the jaws are opened. The suture loops, which are threaded through both links 296, 298 of the delivery device 232, are passed over and around the base of the LAA. The rotation adapter 240, first articulation knob 242, and second articulation knob 244 are used to position both links 296, 298 parallel to the long axis of the LAA os, or opening, if an eccentric or elliptical shaped os is present. With the flat surfaces of both links 296, 298 vertical and adjacent to the superior LAA/LA border avoiding contact with the pulmonary artery and L sup. pulmonary vein, the actuator lever 238 is squeezed in a direction 378 towards the handle 236 of the delivery device 232. The first jaw 290 and right second jaw 292 are then closed around the base of the left atrial appendage, while avoiding squeezing or "milking" a potential blood clot from the LAA pocket or its mural attachment. Further care should be taken to avoid enclosing or clamping circumflex artery or coronary venous structures. FIG. 13B shows the orientation and appearance of the delivery device 232 when in a closed position. With both links 296, 298 generally aligned with the perimeter of the os and snug up against the edge of the LAA, one of the top suture locks 260, 262 are tightened to tighten the suture and to secure the links into position. The second of the two top suture locks 260, 262 is then are tightened to tighten the suture and to doubly secure the links 296, 298 together. Adequate positioning of the links is verified via visual and/or video inspection and echosonography. Once positioned, a titanium fastener is placed on each of the sutures holding the links 296, 298 in place. Alternatively, hand-tied knots or other fastening means may be used. The remaining two sutures tethering the links 296, 298 to the jaws 290, 292 of the delivery device are then removed. Finally, the delivery device 232 is removed from the surgical field. While the general steps of the use of the delivery device 232 of FIG.

11 are described, they may be performed in differing order per the surgeon's preference or the dictates of the surgical field.

Figure 14A:
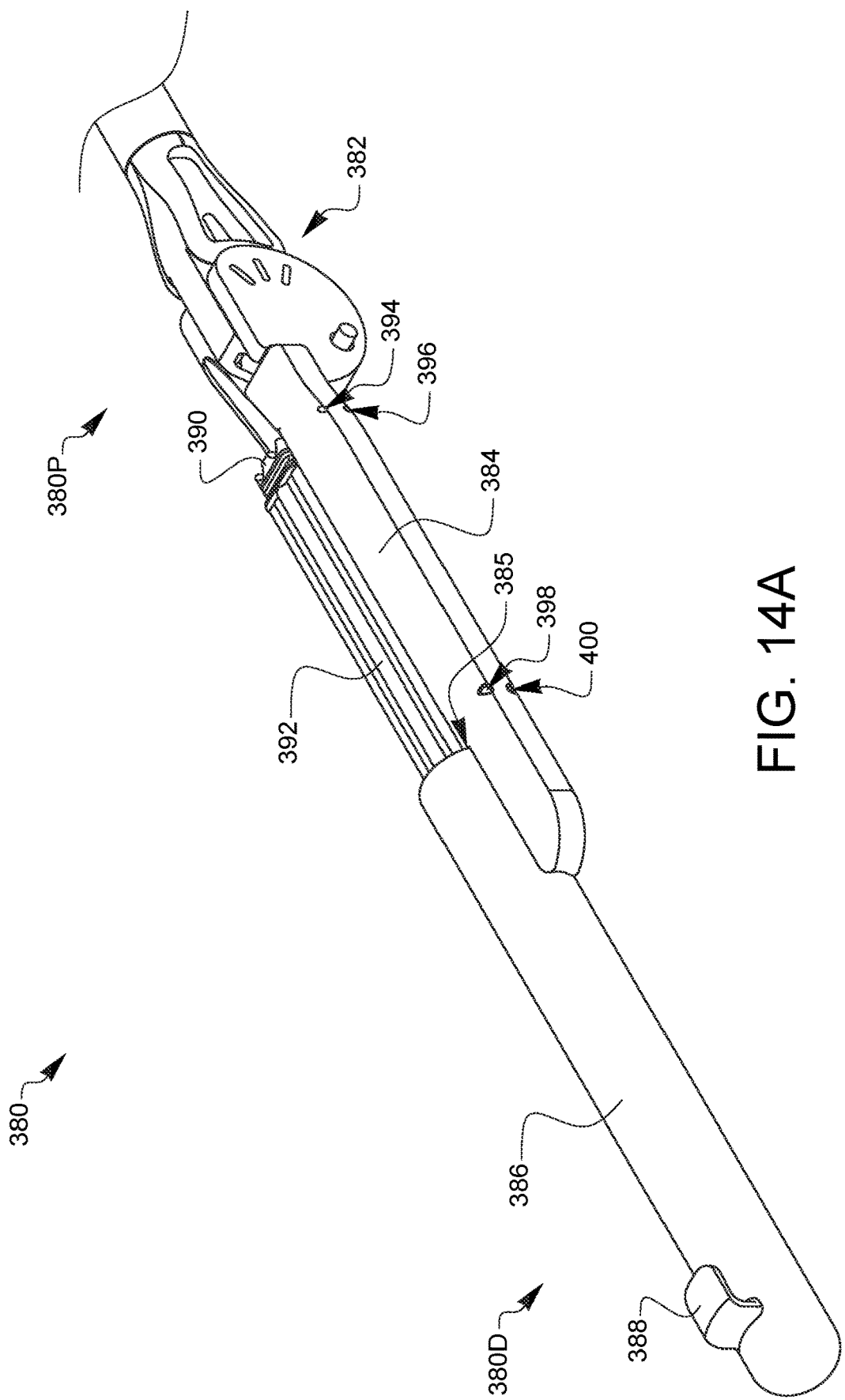
FIGS. 14A and 14B are top-left-front and bottom-left-front perspective views, respectively of an alternate embodiment of a distal tip of a delivery device for a minimally invasive occlusion device.
Figure 14B:
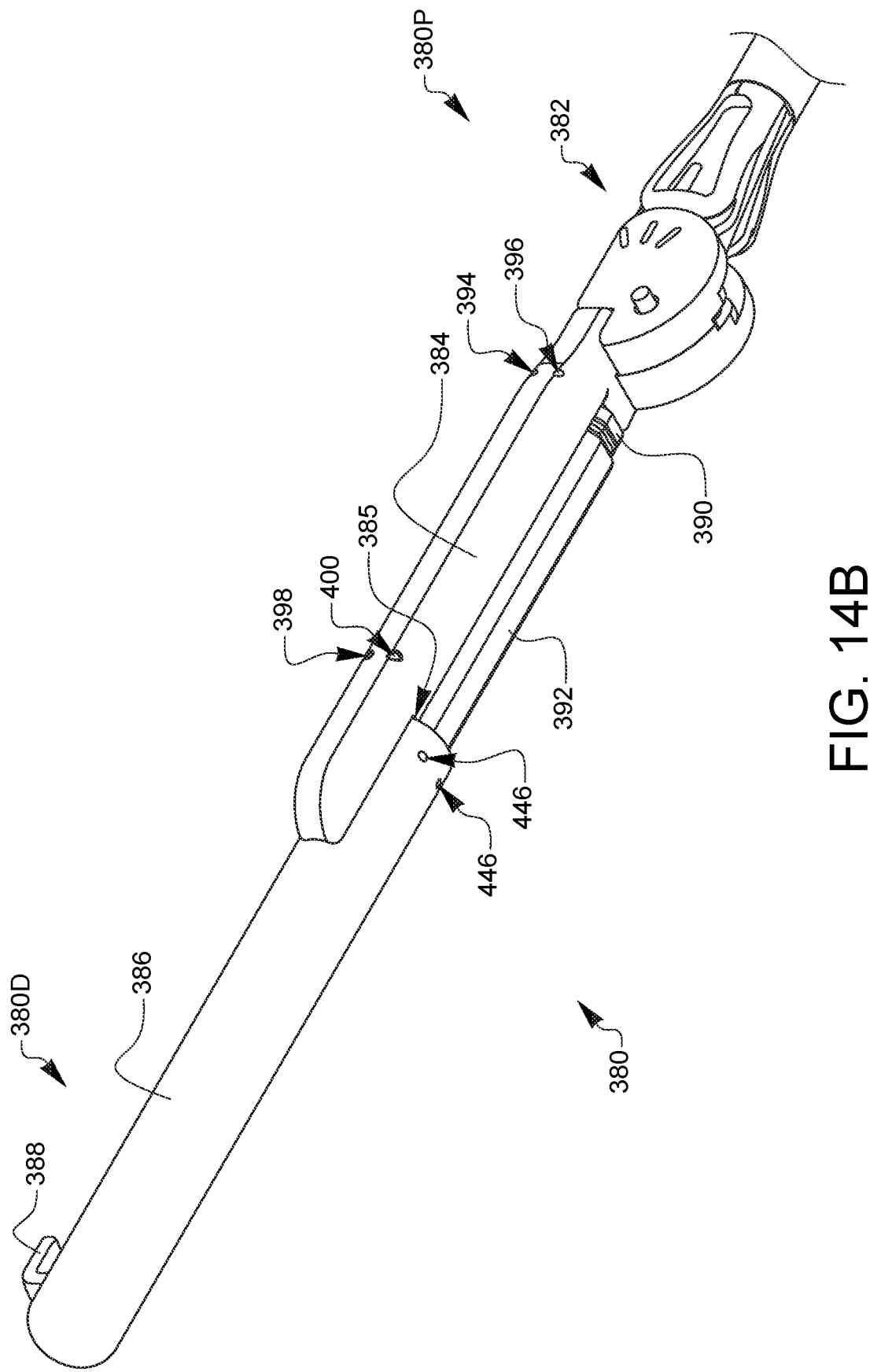

FIGS. 14A and 14B are top-left-front and bottom-left-front perspective views, respectively of an alternate embodiment of a distal tip of a delivery device for a minimally invasive occlusion device. FIGS. 14A and 14B illustrate the introducer device having an introducer sheath distal tip 380 for introducing or delivering an occlusion device for a left atrial appendage. In view is a second articulation joint 382 of an instrument similar to the delivery device 232 illustrated and described in regard to FIGS. 11-13B. Connected to the second articulation joint 382 is a cradle 384 for holding a first link 390 which is covered by a sheath 392. The cradle 384 further defines several suture apertures 394, 396, 398, 400, which are configured to thread suture through for the purpose of tethering and securing the first link 390 to the cradle 384. Towards the distal end 380D of the introducer sheath distal tip 380 is a deployment cap 386 which defines a hook 388. The cylindrical deployment cap 386 may also be referred to as a sheath or a cylindrical cap. This deployment cap 386 is placed over a second link, which is not visible in this view, and part of the first link 390. FIG. 14B is a bottom-left-front perspective view of the introducer sheath distal tip 380 of FIG. 14A, showing the deployment cap suture apertures 446, which are configured to thread suture therethrough for the purpose of securing the deployment cap to the introducer sheath distal tip 380. A cradle stop 385 is defined by the cradle 384 for the purpose of limiting insertion depth of the deployment cap 386 over the first link 390.

Figure 15B:
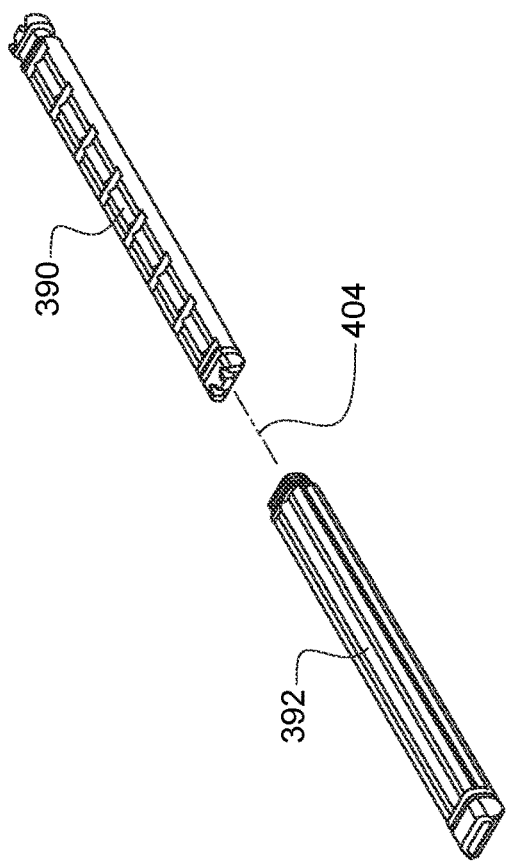
FIG. 15A-15C are a series of exploded views illustrating the assembly of the distal tip of the delivery device of FIGS. 14A and 14B.
Figure 15A:
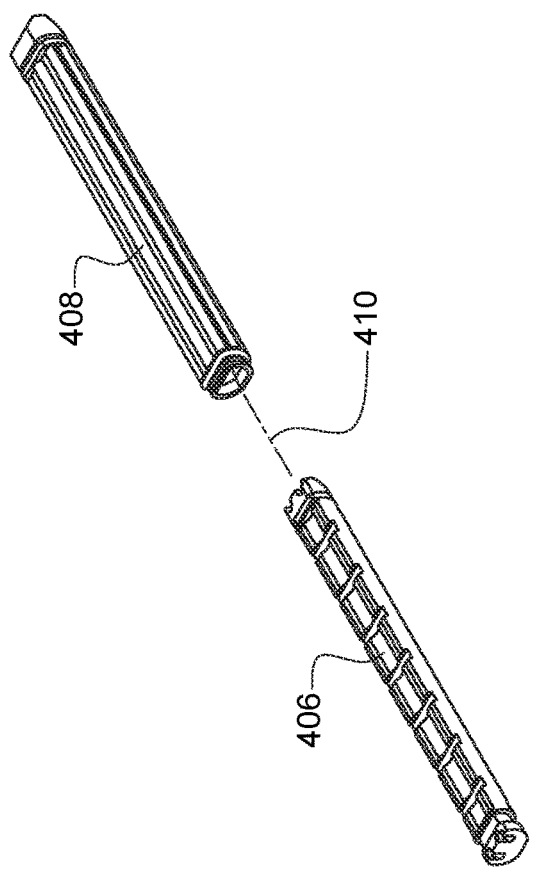
Figure 15C:
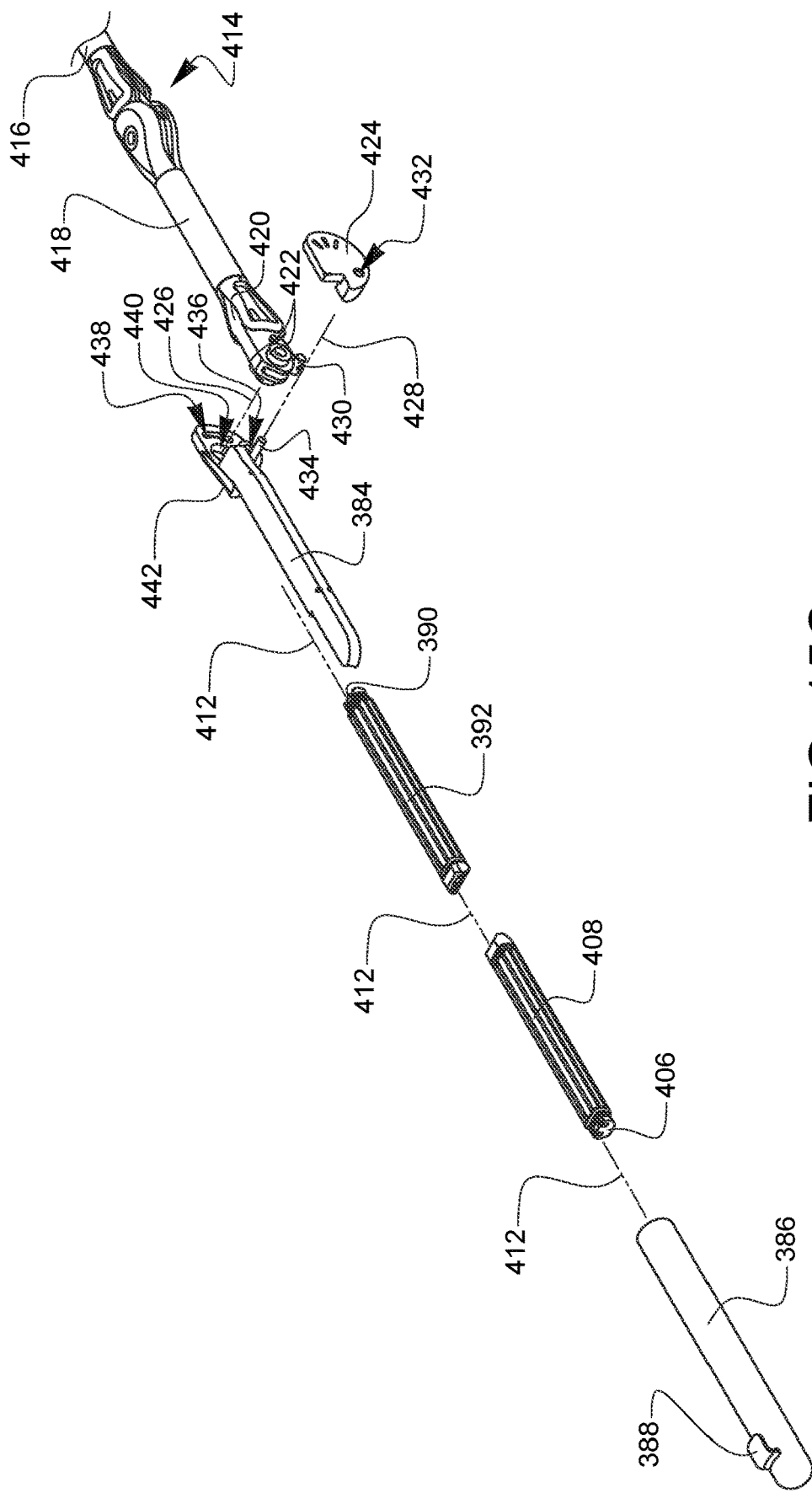

FIG. 15A-15C are a series of exploded views illustrating the assembly of the distal tip of the delivery device of FIGS. 14A and 14B. FIG. 15A shows the insertion of a second mobile link 406 into a sheath 408 along axis 410. FIG. 15B shows the insertion of a first tethered link 390 into a sheath 392 along axis 404. FIG. 15C illustrates the remaining assembly steps of the distal tip of the delivery device of FIGS. 14A and 14B. Coupled to a shaft 416 is a first articulation joint 414, a secondary shaft 418 coupled to the first articulation joint 414, and a hinge 420 coupled to the secondary shaft 418. The hinge 420 further defines two axles 422 and has a barrel 430 protruding from its end. A housing cover 424 further defines a hole 432. The housing cover 424 is placed along axis 428 onto axle 422. The cradle 384 further defines a housing portion 442, a post 434, a hole 436, a slot 438, and a recess 440. The cradle is placed along axis 428 onto axle 422, with the recess 440 mating with the axle 422, the post 434 mating with the hole 432 on the housing cover 424, and the slot 438 mating with the hinge 420. Next, the first link 390 with sheath 392 is placed onto cradle 384 along axis 412, and the mobile link 406 with sheath 408 is placed end to end with the first link 390 along axis 412. Finally, the deployment cap 386 is placed onto end of mobile link 406 and first link 390 along axis 412. While not shown in this view, the first link 390 is tethered to the cradle 384 with filament or suture, and the deployment cap 386 is also tethered to the cradle 384 with filament or suture. It should be noted that the introducer sheath distal tip 380 is arranged and configured such that the links 390, 406 are loaded into the cradle 384 end to end, resulting in a straight or 180-degree position relative to one another. Upon deployment and use of the introducer sheath distal tip 380, the links 390, 406 are pivoted towards each other, such that the positional angle between the links 390, 406 becomes more acute until closure around tissue such as the left atrial appendage provides some resistance. At this time, the compensating coupler mechanism allows for the folded portion or joined portion of the two links 390, 406 to accommodate a variety of anatomical variations and sizes of tissue structures being occluded. This feature provides a parallel, near parallel, or substantially parallel closure of the two links 390, 406 around a left atrial appendage or other tissue structure when tightened by a filament or suture independent of the introducer sheath distal tip 380.

Figure 16A:
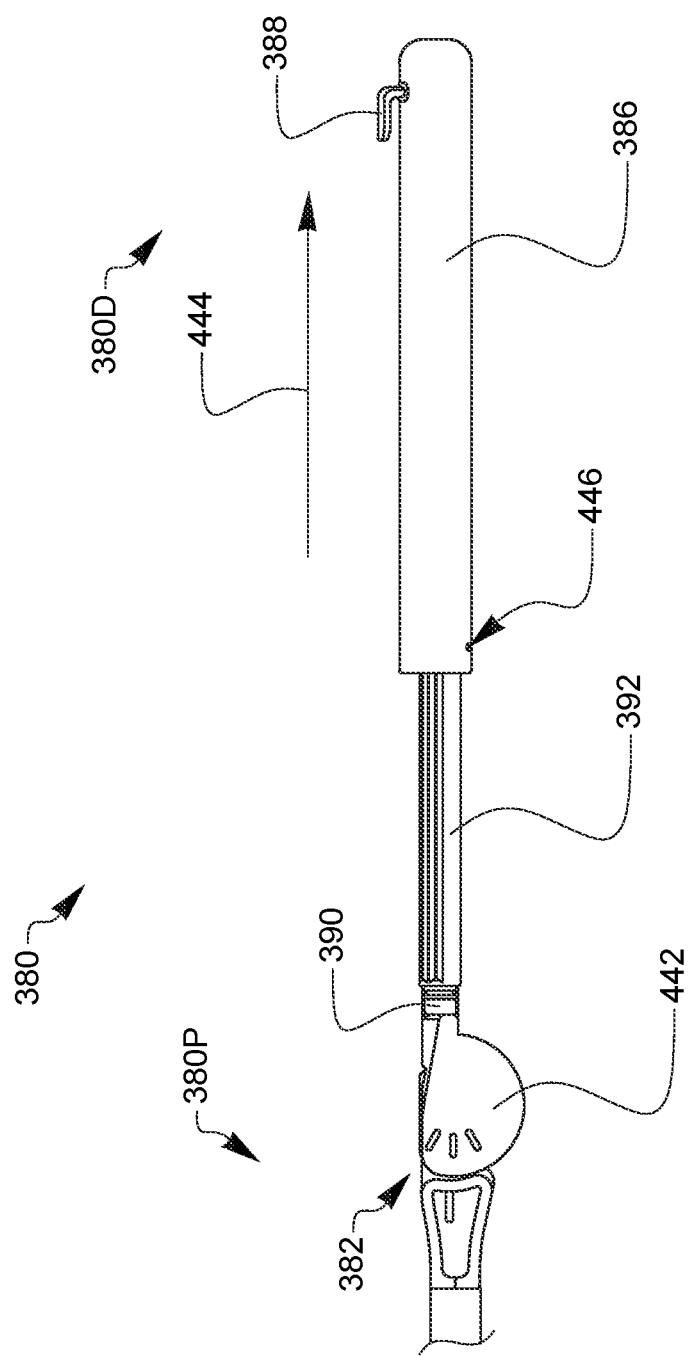
FIG. 16A-16C are side views illustrating the operational principles of the distal tip of the delivery device of FIGS. 14A and 14B.
Figure 16B:
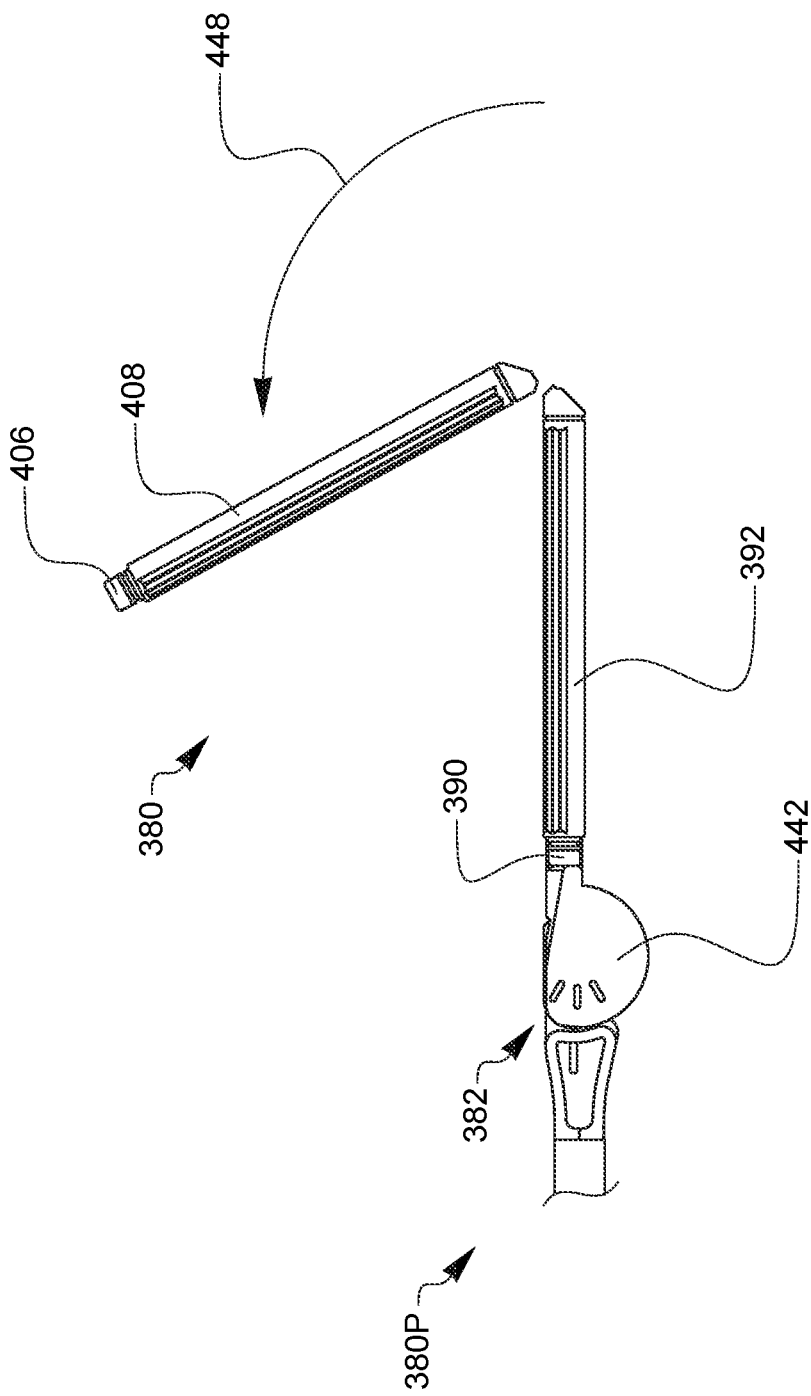
Figure 16C:
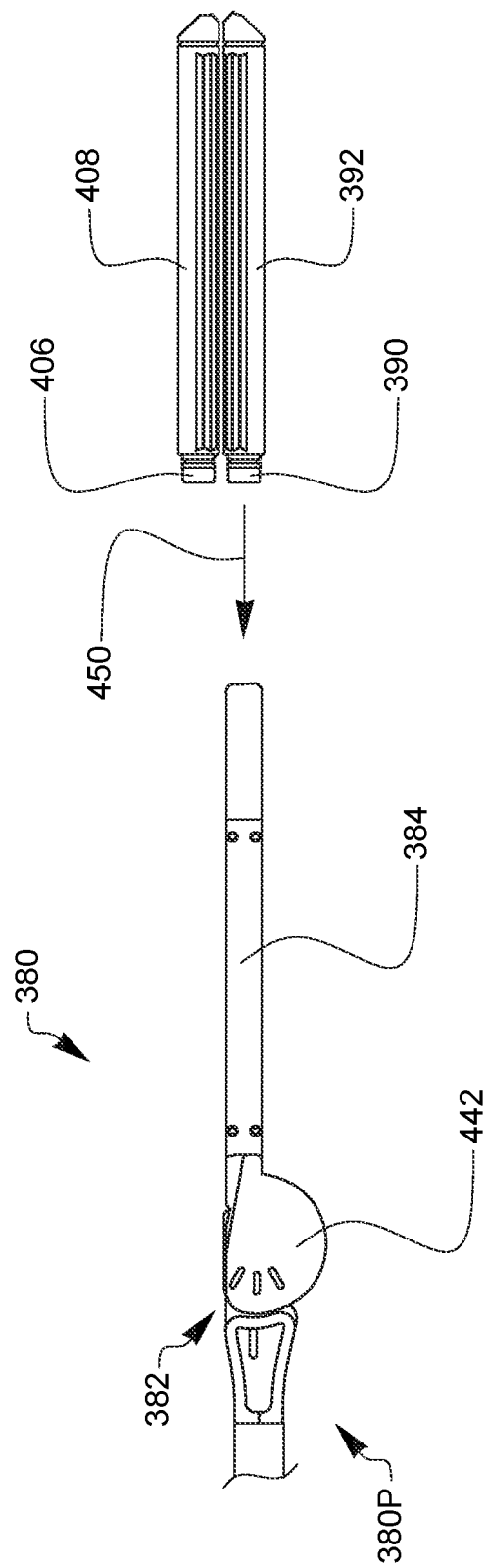

FIG. 16A-16C are side views illustrating the operational principles of the distal tip of the delivery device of FIGS. 14A and 14B. While illustrated in the absence of live tissue, the procedure is similar to those previously described in regard to FIGS. 8A-8I. In a minimally invasive surgical procedure for occlusion of the left atrial appendage, introducer sheath distal tip 380 is used to deliver an occlusion to the base of the left atrial appendage (LAA) when on the distal end of a minimally invasive surgical device. In a procedure utilizing a right lateral mini-thoracotomy access to the beating or arrested heart and great vessels can be obtained and the left atrial appendage exposed through the transverse sinus. A grasper or other suitable surgical instrument is used to hold the LAA and facilitate occlusion using the introducer sheath distal tip 380. The introducer sheath distal tip 380 is passed superior to the base of the LAA while the LAA is being grasped or held in place. A second grasper may be positioned inferior to the LAA to grasp the hook 388 on the fixed introducer sheath distal tip 380. There are two suture locks, not shown herein, that hold the deployment cap 386 onto the end of the introducer sheath distal tip 380 by threading sutures through the deployment cap suture apertures 446. The suture locks are unlocked, releasing the deployment cap 386 which is then slid along with its captured suture axially off of the mobile link 406 in direction 444 towards the distal end 380D of the introducer sheath distal tip 380, as illustrated in FIG. 16A. The deployment cap 386 is then removed from the surgical field along with the captured sutures. The captured sutures, the other ends of which are threaded through the tethered link 390 and the mobile link 406, are released from the deployment cap suture apertures 446 in the deployment cap 386.

The flat surface of the tethered link 390 is placed vertical and adjacent superior to the base of the left atrial appendage, avoiding contact with the pulmonary artery and left superior pulmonary vein. The device shaft rotation and angular FIG. 16A-16C are side views illustrating the operational principles of the distal tip of the delivery device of FIGS. 14A and 14B. While illustrated in the absence of live tissue, the procedure is similar to those previously described. In a minimally invasive surgical procedure for occlusion of the left atrial appendage, introducer sheath distal tip 380 is used to deliver an occlusion to the base of the left atrial appendage (LAA) when on the distal end of a minimally invasive surgical device. In a procedure utilizing a right lateral mini-thoracotomy access to the beating or arrested heart and great vessels can be obtained and the left atrial appendage exposed through the transverse sinus. A grasper or other suitable surgical instrument is used to hold the LAA and facilitate occlusion using the introducer sheath distal tip 380. The introducer sheath distal tip 380 is passed superior to the base of the LAA while the LAA is being grasped or held in place. A second grasper may be positioned inferior to the LAA to grasp the hook 388 on the fixed introducer sheath distal tip 380. There are two suture locks, not shown herein, that hold the deployment cap 386 onto the end of the introducer sheath distal tip 380 by threading sutures through the deployment cap suture apertures 446. The suture locks are unlocked, releasing the deployment cap 386 which is then slid along with its captured suture axially off of the mobile link 406 in direction 444 towards the distal end 380D of the introducer sheath distal tip 380, as illustrated in FIG. 16A. The deployment cap 386 is then removed from the surgical field along with the captured sutures. The captured sutures, the other ends of which are threaded through the tethered link 390 and the mobile link 406, are released from the deployment cap suture apertures 446 in the deployment cap 386.

adjustment options are used to position the tethered link 390 parallel to the long axis of the left atrial appendage os if an eccentric or elliptical shaped os is present. The mobile link 406 is pulled and positioned around the opposite side of the LAA under the grasper. Using a second grasper, the mobile link 406 is positioned across from the tethered link 390 and brought around the LAA in a direction 448 while avoiding squeezing or "milking" a potential blood clot from the LAA pocket or its mural attachment. This arrangement of the tethered link 390 and mobile link 406 is illustrated in FIG. 16B. During this procedural step it is important to avoid enclosing or clamping circumflex artery or coronary venous structures. Once both links 390, 406 are generally aligned with the perimeter of the left atrial appendage os and snug up against the edge of the LAA, one of the sutures threaded through the links 390, 406 is tightened to secure the links into position. The second suture is then tightened to doubly secure the links 390, 406 together, as illustrated in FIG. 16C. Adequate positioning of the links is verified via visual and/or video inspection and echosonography. At this point, if re-positioning is required, the sutures may be loosened, and the links 390, 406 re-positioned as desired. Once positioned, a titanium fastener is placed on each of the sutures holding the links 390, 406 in place. Alternatively, hand-tied knots or other fastening means may be used. The remaining suture tethering the tethered link 390 to the cradle 384 is then removed. Finally, the introducer sheath distal tip 380 is removed from the surgical field in direction 450, as illustrated in FIG. 16C. While the general steps of the use of a delivery device having an introducer sheath distal tip 380 like the one shown in FIGS. 14A and 14B is described, the steps may be performed in differing order per the surgeon's preference or the dictates of the surgical field.

Various advantages of a minimally invasive occlusion device and related methods have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A minimally invasive surgical assembly comprising:
    an occlusion device for occluding a left atrial appendage of a patient, the occlusion device comprising:
        an elongated first link comprising a first end and a second end; and
        an elongated second link comprising a first end and a second end, wherein the first end of the second link is pivotably coupled to the first end of the first link; and
    a delivery device, the delivery device comprising a rigid frame having a receiving aperture that extends through a first portion of the rigid frame, the receiving aperture adapted to receive at least a portion of the left atrial appendage of the patient, the receiving aperture being at least partially defined by a first aperture edge and a second aperture edge,
    wherein the first link of the occlusion device is configured to be removably coupled to a second portion of the rigid frame that is at or adjacent to the first aperture edge, and the second link of the occlusion device is configured to be removably coupled to a third portion of the rigid frame that is at or adjacent to the second aperture edge,
    wherein each of the first link and the second link are substantially linear, and wherein when the first link is removably coupled to the first portion of the rigid frame and the second link is removably coupled to the second portion of the rigid frame, the first link and the second link form an acute angle, and
    wherein a fourth portion of the rigid frame that entirely surrounds the receiving aperture is planar, and wherein the fourth portion of the rigid frame is at least partially defined by a first perimeter edge that is parallel to the first aperture edge and a second perimeter edge that is parallel to the second aperture edge.

2. The minimally invasive surgical assembly of claim 1, wherein the rigid frame is planar.

3. The minimally invasive surgical assembly of claim 1, wherein each of the first aperture edge and the second aperture edge is substantially linear, and the first link is configured to be parallel to the first aperture edge and the second link is configured to be parallel to the second aperture edge.

4. The minimally invasive surgical assembly of claim 3, wherein the receiving aperture is at least partially defined by the first aperture edge, the second aperture edge, and a third aperture edge, and the third aperture edge is substantially linear.

5. The minimally invasive surgical assembly of claim 1, wherein the rigid frame is translucent or transparent.

* * * * *